United States Patent
Ye et al.

(10) Patent No.: US 11,447,784 B2
(45) Date of Patent: Sep. 20, 2022

(54) METHOD FOR IMPROVING TRANSFORMATION EFFICIENCY OF PLANT AND METHOD FOR TRANSFORMING PLANT

(71) Applicants: INSTITUTE OF CROP SCIENCE, CHINESE ACADEMY OF AGRICULTURAL SCIENCES, Beijing (CN); JAPAN TOBACCO INC., Tokyo (JP)

(72) Inventors: Xingguo Ye, Beijing (CN); Ke Wang, Beijing (CN); Yuji Ishida, Shizuoka (JP); Chizu Yanagihara, Shizuoka (JP); Huiyun Liu, Beijing (CN); Kunyang Wang, Beijing (CN); Lei Shi, Beijing (CN); Lipu Du, Beijing (CN); Jing Wang, Beijing (CN); Zhishan Lin, Beijing (CN)

(73) Assignees: INSTITUTE OF CROP SCIENCE, CHINESE ACADEMY OF AGRICULTURAL SCIENCES, Beijing (CN); KANEKA CORPORATION, Osaka (JP)

(*) Notice: Subject to any disclaimer, the term of this patent is extended or adjusted under 35 U.S.C. 154(b) by 0 days.

(21) Appl. No.: 16/617,930

(22) PCT Filed: Jun. 7, 2018

(86) PCT No.: PCT/CN2018/090239
§ 371 (c)(1),
(2) Date: Nov. 27, 2019

(87) PCT Pub. No.: WO2018/224001
PCT Pub. Date: Dec. 13, 2018

(65) Prior Publication Data
US 2020/0231977 A1   Jul. 23, 2020

(30) Foreign Application Priority Data

Jun. 7, 2017 (CN) .......................... 201710422896.6

(51) Int. Cl.
*C12N 15/82* (2006.01)
*C07K 14/415* (2006.01)

(52) U.S. Cl.
CPC ........ *C12N 15/8201* (2013.01); *C07K 14/415* (2013.01); *C12N 15/8216* (2013.01)

(58) Field of Classification Search
None
See application file for complete search history.

(56) References Cited

U.S. PATENT DOCUMENTS

2006/0123505 A1   6/2006   Kikuchi et al.
2010/0293662 A1   11/2010  Ji et al.
(Continued)

FOREIGN PATENT DOCUMENTS

CN    103224563 A   *   7/2013
CN    106676128 A       5/2017
(Continued)

OTHER PUBLICATIONS

Zhao, P. "Cloning and Function Analysis of Several Genes Relevant to Agrobacterium-Mediated Transformation and Tissue Culture Regeneration in Wheat". Dissertation, Chinese Academy of Agricultural Sciences. (Year: 2015).*
(Continued)

*Primary Examiner* — Matthew R Keogh
*Assistant Examiner* — David R Byrnes
(74) *Attorney, Agent, or Firm* — Birch, Stewart, Kolasch & Birch, LLP.

(57) ABSTRACT

The present invention provides a method for improving transformation efficiency of a plant. The method according
(Continued)

to the present invention comprises the use of a nucleic acid encoding the amino acid sequence set forth in SEQ ID NO: 2 or 4, or a nucleic acid encoding a polypeptide comprising an amino acid sequence having at least 85% identity with the amino acid sequence set forth in SEQ ID NO: 2 or 4, and having a function of improving transformation efficiency of a plant.

2 Claims, 5 Drawing Sheets

Specification includes a Sequence Listing.

(56) References Cited

U.S. PATENT DOCUMENTS

| | | | |
|---|---|---|---|
| 2013/0091599 A1 | 4/2013 | Takakura et al. | |
| 2014/0130203 A1 | 5/2014 | La Rosa et al. | |
| 2017/0121722 A1* | 5/2017 | Anand | C07K 14/415 |

FOREIGN PATENT DOCUMENTS

| | | |
|---|---|---|
| JP | 2010-166924 A | 8/2010 |
| WO | WO 01/23575 A2 | 4/2001 |
| WO | WO 01/23575 A3 | 4/2001 |
| WO | WO 2005/063990 A2 | 7/2005 |
| WO | WO 2005/063990 A3 | 7/2005 |
| WO | WO 2007/094762 A2 | 8/2007 |
| WO | WO 2307/148819 A1 | 12/2007 |
| WO | WO 2010/086221 A1 | 8/2010 |
| WO | WO 2017/074547 A1 | 5/2017 |

OTHER PUBLICATIONS

Zhao, S., et al., "Characterization and expression analysis of WOX5 genes from wheat and its relatives", Gene. 2014. 537(1):63-69 (Year: 2014).*

Guo et al. Proc. Natl. Acad. Sci. USA 101: 9205-9210 (Year: 2004).*

Lowe et al. "Morphogenic Regulators Baby boom and Wuschel Improve Monocot Transformation". The Plant Cell. 28: 1998-2015. (Year: 2016).*

Aguan et al., "Low-temperature-dependent expression of a rice gene encoding a protein with a leucine-zipper motif," Molecular & General Genetics, vol. 240, No. 1, Jul. 1993, pp. 1-8.

Barcelo et al., "Transformation of Cereals by Microprojectile Bombardment of Immature Inflorescence and Scutellum Tissues," Methods in Molecular Biology, vol. 49 Plant Gene Transfer and Expression Protocols, 1995, pp. 113-123.

Extended European Search Report for European Application No. 18813480.3, dated Dec. 1, 2020.

Graaff et al., "The WUS homeobox-containing (WOX) protein family," Genome Biology, vol. 10, 2009, pp. 248.1-248.9.

Gupta et al., "Upstream sequence of fatty acyl-CoA reductase (FAR6) of *Arabidopsis thaliana* drives wound-inducible and stem-specific expression," Plant Cell Rep, vol. 31, 2012 (published online Dec. 22, 2011), pp. 839-850.

Hardwood, "Advances and remaining challenges in the transformation of barley and wheat," Journal of Experimental Botany, vol. 63, No. 5, 2012, pp. 1791-1798.

Ikeuchi et al., "Plant Callus: Mechanisms of Induction and Repression," The Plant Cell, vol. 25, Sep. 2013, pp. 3159-3173.

International Search Report and Written Opinion of the International Searching Authority for International Application No. PCT/CN2018/090239, dated Aug. 31, 2018.

Ishida et al., "*Agrobacterium*-mediated transformation of maize," Nature Protocols, vol. 2, No. 7, 2007 (published online Jun. 21, 2007), pp. 1614-1621.

Ishida et al., "Wheat (*Triticum aestivum* L.) Transformation Using Immature Embryos," Agrobacterium Protocols: vol. 1, Methods in Molecular Biology, vol. 1223, 2015, pp. 189-198.

Komari et al., "Vectors carrying two separate T-DNAs for co-transformation of higher plants mediated by *Agrobacterium tumefaciens* and segregation of transformants free from selection markers," The Plant Journal, vol. 10, No. 1, 1996, pp. 165-174.

Komori et al., "Map-based cloning of a fertility restorer gene, Rf-1, in rice (*Oryza sativa* L.)," The Plant Journal, vol. 37, 2004, pp. 315-325.

Medvecká et al., "Wheat (*Triticum aestivum* L.) Transformation Using Mature Embryos," in Agrobacterium Protocols: vol. 1, Methods in Molecular Biology, vol. 1223, 2015, pp. 199-209.

Mundy et al., "Nuclear proteins bind conserved elements in the abscisic acid-responsive promoter of a rice rab gene," Proc. Natl. Acad. Sci. USA, vol. 87, Feb. 1990, pp. 1406-1410.

Ohshima et al., "Analysis of Stress-Induced or Salicylic Acid-Induced Expression of the Pathogenesis-Related 1a Protein Gene in Transgenic Tobacco," The Plant Cell, vol. 2, Feb. 1990, pp. 95-106.

Richardson et al., "Efficient *Agrobacterium* transformation of elite wheat germplasm without selection," Plant Cell Tiss. Organ. Cult, vol. 119, 2014 (published online Jul. 11, 2014), pp. 647-659.

Schulze-Lefert et al., "Inducible in vivo DNA footprints define sequences necessary for UV light activation of the parsley chalcone synthase gene," The EMBO Journal, vol. 8, No. 3, 1989, pp. 651-656.

Shinozaki et al., "Molecular responses to dehydration and low temperature differences and cross-talk between two stress signaling pathways," Current Opinion in Plant Biology, vol. 3, 2000, pp. 217-223.

Van Breusegem et al., "Heat-inducible rice hsp82 and hsp70 are not always co-regulated," Planta, vol. 193, 1994, pp. 57-66.

Walker et al., "DNA sequences required for anaerobic expression of the maize alcohol dehydrogenase 1 gene," Proc. Natl. Acad. Sci. USA, vol. 84, Oct. 1987, pp. 6624-6628.

Wang et al., "Effect of Fertilizer Application on Yield and Population of Strong Gluten Wheat Xinong 979," Acta Agriculturae Boreali-occidentalis Sinica, vol. 21, No. 6, 2012, pp. 63-66, with an English abstract.

Wang et al., "Generation of marker-free transgenic hexaploid wheat via an *Agrobecterium*-mediated co-transformation strategy in commercial Chinese wheat varieties," Plant Biotechnology Journal, vol. 15, 2017, pp. 614-623.

Xu et al., "Characterization of a rice gene family encoding root-specific proteins," Plant Molecular Biology, vol. 27, 1995, pp. 237-248.

Xu et al., "Regulation, espression and function of a new basic chitinase gene in rice (*Oryza sativa* L.)," Plant Molecular Biology, vol. 30, 1996, pp. 387-401.

Yin et al., "Construction and Validation of Three Convenient and Practical Constructs for Plant Transformation," Journal of Plant Genetic Resources, vol. 15, No. 6, 2014, pp. 1327-1333, with an English abstract.

Zuo et al., "The WUSCHEL gene promotes vegetative-to-embryonic transition in *Arabidopsis*" The Plant Journal, vol. 30, No. 3, 2002, 349-359.

* cited by examiner

METHOD FOR IMPROVING TRANSFORMATION EFFICIENCY OF PLANT AND METHOD FOR TRANSFORMING PLANT

TECHNICAL FIELD

The present invention relates to a method for improving transformation efficiency of a plant and a method for transforming a plant.

The present invention also relates to a nucleic acid construct. The nucleic acid construct according to the present invention can be used in a method for improving transformation efficiency of a plant or a method for transforming a plant.

The present invention further relates to transformed plant.

The present invention further relates to an application of a wheat TaWox5 gene in improving the transformation efficiency of monocot, especially wheat, maize and rice.

BACKGROUND ART

Since the success of plant transgene technology in 1983, the use of genetic engineering approach to improve plants has grown very fast. In 2016, a total of 28 countries in the world planted transgenic crops with an area of 179.7 million hectares and an increase of about 100 times over 1996, and about 18 million farmers benefited from the cultivation of transgenic crops. The cultivation of the transgenic crops not only increased yields, increased incomes, but also reduced the use of pesticides, protected the environment and biodiversity, and improved the quality of agricultural products. However, transgenic crops commercially planted all over the world at present are only limited to insect-resistant corns and cottons, herbicide-resistant soybeans and rapes, antivirus papaya, etc., and there are no wheat and other major cereal grain crops. In contrast, global transgenic wheat research and industrialization are clearly in a backward state. In addition to the limitations of the safety, industrial policies, people's understanding, and genetic functions of transgenic varieties, the inefficient genetic transformation technique is the main link that limits the research and development of transgenic wheat (Harwood, (2012) J. Exp. Bot. March; 63(5):1791-8.). In order to cultivate transgenic wheat with disease resistance, drought tolerance, salt tolerance, high quality and efficient nutrient uptake, it is necessary to identify the functions of a large number of candidate genes. Because the target gene expression is affected by factors such as insertion sites and insertion copy number, as well as exogenous gene insertion to the inheritance and functions of endogenous gene, it is necessary to obtain a certain number of transgenic plants in order to identify the functions of each candidate gene. In addition, with the completion of wheat genome sequencing work, a large number of genes will be cloned and subject to functional research. Therefore, it is urgently required to improve the transformation efficiency of wheat, expand the transformation scale, establish an efficient, safe and large-scale transgenic technology system and promote the industrialization of transgenic wheat and the functional genomics research process of wheat because transgenic wheat research and development and wheat functional genomics research require a large number of transgenic plants.

Among the main crops, wheat is a crop difficult for genetic transformation (Harwood, 2012). The genetic transformation efficiency is low and the reproducibility is poor. The process of genetic engineering breeding is obviously lagging behind that of crops such as soybean, maize, cotton and rice. It is known that Japan Tobacco Inc. has significantly increased the genetic transformation efficiency of wheat in recent years, and Australia can use this technology to improve the transformation efficiency of wheat by about 40% (Richardson et al., (2014) Plant Cell Tiss. Organ. Cult.; 64(1):1-19). But this technology has effects only on Fielder, Westonia and a few genotypes, a majority of wheat varieties is still low in transformation efficiency or even cannot be transformed. This unit introduced this technology in 2014. By means of the digestion, absorption and improvement on the technology, the transformation efficiency of wheat genotype Fielder and CB037 also reaches 40%, and 15 commercial varieties, such as Zhoumai 18, Yangmai 16 and Ji 5264 are successfully transformed. However, except that the transformation efficiency of Kenong 199 reaches 20%, the transformation efficiency of other varieties is not high, in which the transformation efficiency of Jimai 22 is only 2.7%, the transformation efficiency of Zhongmai 895 is only 3.6%, and Aikang 58 and Jing 411 may not be transformed successfully. In view of the industrialization prospect of transgenic wheat, breeders need to use wheat varieties which are promoted in a large area as transformation receptors, and therefore, the transformation of the commercial wheat varieties is the biggest limiting factor.

The WUSCHEL genes (WUS genes) are homeodomain transcription factors that improve or suppress expression of other genes. It is known that most of them are expressed unsymmetrically along the embryonic apical-basal axis. Plural genes having the WUS homeobox have been found in various plants and such genes are called WOX.

The WUS/WOX is considered to play an important role in the maintenance of shoot stem cells in early development. The WUS/WOX has been found in many plants including *Arabidopsis*, petunia, corn, and rice.

The document, Graaff et al. (Genome Biology, 2009, 10, 248) is a review of the WOX family. 14 members of the WOX family, WOX1 to WOX14, are listed in the document. Among the WOX family members, WOX5 was originally identified in rice and considered to be involved in the lateral root formation and the shoot formation in early development. It plays an important role in the maintenance of stem cells. Since differentiation of cells prevents further elongation in the meristem (root cap, shoot apical) in particular, cells in such parts are maintained with differentiation suppressed (maintenance of stem cells) to allow further growth and genes responsible for the maintenance are considered to be WUX.

The possibility that WUS/WOX promotes callus formation in the somatic embryogenesisis has been suggested (e.g., Ikeuchi et al., The Plant Cell, 2013, 25, 3159-3173). However, it has been reported that overexpression of WUS/WOX alone results in negative phenomena, even death of callus, lack of redifferentiation, or abnormal morphologies failing to develop into normal individuals (Plant Journal, 30 (3), 2000). Therefore, measures such as control of WUS/WOX gene expression in an inducible promoter, introduction of a nucleic acid other than the desired nucleic acid to be expressed, such as BBM (Baby Boomer), or removal of the WUS/WOX gene at the time when it becomes unnecessary have been carried out.

Besides wheat mentioned above, for example, soybean, kidney bean, red pepper, and the like are difficult to culture and considered to be, so-called, "difficult-to-culture" species. Moreover, even in a species, there are varieties (for example, B73 of corn) that are more difficult to culture in comparison with general research varieties (for example, A188 in the case of corn). There are no effective methods obtained for efficiently transforming plants, in particular, plants or varieties considered to be "difficult-to-culture" to obtain transformed plants and development of such a method has been desired.

CITATION LIST

Patent Literature

PTL 1: JP 2010-166924 A
PTL 2: WO2007/148819

Non-Patent Literature

NPL 1: Harwood, (2012) J. Exp. Bot. March; 63(5):1791-8
NPL 2: Richardson et al., (2014) Plant Cell Tiss. Organ. Cult 119, 647-659
NPL 3: Graaff et al., (2009) Genome Biology 10, 248
NPL 4: Ikeuchi et al., (2013) The Plant Cell 25, 3159-3173
NPL 5: Plant Journal 30(3) 2000
NPL 6: Xu et al., (1996) Plant Mol. Biol. 30: 387
NPL 7: Ohshima et al, (1990) Plant Cell 2:95
NPL 8: Aguan et al., (1993) Mol. Gen. Genet. 240:1
NPL 9: Van Breusegem et al., (1994) Planta 193:57
NPL 10: Nundy et al., (1990) Proc. Natl. Acad. Sci. USA 87:1406
NPL 11: Schulze-Lefert et al., (1989) EMBO J. 8:651
NPL 12: Walker et al., (1987) Proc. Natl. Acad. Sci. USA 84:6624
NPL 13: Shinozaki, K. and Yamaguchi-Shinozaki, K., (2000) Curr. Opin. Plant Biol. 3, 217-223
NPL 14: Gupta et al., (2012) Plant Cell Rep. 31: 839-850
NPL 15: Xu et al., (1995) Plant Mol Biol 27: 237-248
NPL 16: Komari et al., (1996) Plant J, 10: 165-174
NPL 17: Komori et al., (2004) Plant J, 37: 315-325
NPL 18: Wang et. al., (2017) Plant biotechnology journal 15:614-623
NPL 19: Rongcheng Wang, Rui Zhang, Acta Agriculturae Boreali-occidentalis Sinica, (2012), 21 (6): 63-66
NPL 20: Ishida, et al., (2015) In Agrobacterium Protocols: Volume 1. Methods in Molecular Biology, vol. 1223 (Wang, K., ed), pp. 189-198. New York: Springer Science+Business Media
NPL 21: Yin Gui-xiang et al., (2014) Journal of Plant Genetic Resources, DOI:10.13430/j.cnki.jpgr.2014.06.022
NPL 22: Barcelo and Lazzeri, (1995) Plant Gene Transfer and Expression Protocols pp 113-123
NPL 23: Medvecká E.et al., (2015), In Agrobacterium Protocols: Volume 1. Methods in Molecular Biology, vol. 1223 (Wang, K., ed), pp. 199-209. New York: Springer Science+Business Media.
NPL 24: Ishida et al., (2007) NATURE PROTOCOLS, Vol. 2, No. 7, 1614-1621

SUMMARY OF INVENTION

Technical Problem

An object of the present invention is to provide an effective method for improving transformation efficiency of a plant and a method for transforming a plant.

Solution to Problem

The present invention includes the following non-limiting embodiments.

Embodiment 1

A method for improving transformation efficiency of a plant, comprising making
1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or
2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant overexpressed in the plant.

Embodiment 2

The method according to embodiment 1, comprising making a nucleic acid encoding a polypeptide comprising an amino acid sequence having an at least 85% identity with the amino acid sequence set forth in SEQ ID NO: 2 or 4 and having a function that improves transformation efficiency of a plant overexpressed in the plant.

Embodiment 3

The method according to embodiment 1 or 2, wherein the plant is a monocotyledon.

Embodiment 4

The method according to any one of embodiments 1 to 3, wherein the plant is selected from the group consisting of corn, wheat, barley, rice, sorghum and rye.

Embodiment 5

The method according to any one of embodiments 1 to 4, wherein the improvement of transformation efficiency of a plant comprises one or more of:
a) improvement of efficiency of callus formation of the plant;
b) improvement of redifferentiation rate of the plant; and
c) improvement of gene transfer efficiency.

Embodiment 6

A nucleic acid construct comprising:
1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or
2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant;
and
a promoter for producing a nucleic acid in the plant.

Embodiment 7

The nucleic acid construct according to embodiment 6, wherein the promoter is a constitutive promoter, an inducible promoter, or a site-specific promoter.

Embodiment 8

A method for transforming a plant, comprising introducing into a plant a nucleic acid construct according to embodiment 6 or 7 and a desired nucleic acid to be expressed in the plant.

Embodiment 9

The method for transformation according to embodiment 8, wherein the nucleic acid construct according to embodiment 6 or 7 or the desired nucleic acid to be produced in the plant is transiently expressed.

Embodiment 10

A transformed plant obtained by the method for transformation according to embodiment 9 or 10.

Embodiment 11

A nucleic acid construct comprising:
1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or
2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant;
a promoter for producing a nucleic acid in the plant; and
a desired nucleic acid to be produced in the plant.

Embodiment 12

The nucleic acid construct according to embodiment 11, wherein
1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or
2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant;
and
a desired nucleic acid to be produced in the plant are connected directly or via a linker.

Embodiment 13

The nucleic acid construct according to embodiment 12, wherein the desired nucleic acid to be produced in the plant is connected to 3' of the nucleic acid 1) or 2).

Embodiment 14

A method for transforming a plant, comprising introducing a nucleic acid construct according to any one of embodiments 11 to 13 into a plant.

Embodiment 15

The method for transformation according to embodiment 14, wherein a nucleic acid construct according to any one of embodiments 11 to 13 is transiently expressed.

Embodiment 16

A transformed plant obtained by the method for transformation according to embodiment 14 or 15.

In other aspects, the present invention also includes the following embodiments.

Embodiment 17

An application of an TaWox5 protein, or a coding gene thereof, or an expression cassette containing said gene, or a recombinant vector containing said gene, or a recombinant bacterium containing said gene in improving the transformation efficiency of a nucleic acid molecule into a target plant.

Embodiment 18

An application of an TaWox5 protein, or a coding gene thereof, or an expression cassette containing said gene in promoting the introduction of a nucleic acid molecule into a target plant.

Embodiment 19

The application according to embodiment 17 or 18, wherein the TaWox5 protein is derived from wheat;
or an amino acid sequence of the TaWox5 protein is SEQ ID NO: 2.

Embodiment 20

The application according to any one of embodiments 17 to 19, wherein,
a coding gene of the TaWox5 protein is DNA molecules as described in any one of the following 1) to 3):
1) DNA molecules in 11825-12573 having a nucleotide sequence of SEQ ID NO. 1;
2) DNA molecules having the homology being greater than 95%, 98%, or 99% with the DNA molecules shown in 1);
3) DNA molecules hybridized under stringent conditions with the DNA sequence defined by 1) and encoded with the same functional polypeptide.

Embodiment 21

The application according to any one of embodiments 17 to 20, wherein,
the plant is wheat.

Embodiment 22

The application according to any one of embodiments 17 to 21, wherein,
the nucleic acid molecule is a plasmid;
or the nucleic acid molecule is a plasmid, and the plasmid is pDE003.

Embodiment 23

A method for improving the transformation efficiency of a nucleic acid molecule into a target plant, comprising the following step of transferring an expression cassette containing a coding gene of an TaWox5 protein and the nucleic acid molecule into the target plant to improve the transformation efficiency of the nucleic acid molecule into the target plant.

Embodiment 24

The method according to embodiment 23, wherein,
the TaWox5 gene is derived from wheat;
a coding gene of the TaWox5 protein is DNA molecules as described in any one of the following 1) to 3):
1) DNA molecules in 11825-12573 having a nucleotide sequence of SEQ ID NO. 1;
2) DNA molecules having the homology being greater than 95%, 98%, or 99% with the DNA molecules shown in 1);
3) DNA molecules hybridized under stringent conditions with the DNA sequence defined by 1) and encoded with the same functional polypeptide;
the expression cassette containing the gene is DNA molecules as described in any one of the following a) to c):
a) DNA molecules in 9812-12837 having a nucleotide sequence of SEQ ID NO. 1;
b) DNA molecules having the homology being greater than 95%, 98%, or 99% with the DNA molecules shown in 1);
c) DNA molecules hybridized under stringent conditions with the DNA sequence defined by 1) and encoded with the same functional polypeptide.

Embodiment 25

The method according to embodiment 23 or 24, wherein,
the plant is wheat;
or the nucleic acid molecule is a plasmid;
or the nucleic acid molecule is a plasmid, and the plasmid is pDE003.

Embodiment 26

The method according to embodiment 25, wherein,
the expression cassette containing the coding gene of the TaWox5 protein and the nucleic acid molecule are transferred to the target plant via the pDE003-TaWox5 vector; the nucleotide sequence of the pDE003-TaWox5 vector is SEQ ID NO. 1.

Advantageous Effects of Invention

In the present invention, the transformation efficiency (callus formation/redifferentiation efficiency) of plants was improved only by overexpressing the nucleic acid 1) or 2), which is a WOX5-related gene, without conducting expression of another gene such as BBM genes, other than the gene of interest, control of expression or eliminate or remove the WOX5-related gene. In particular in wheat, callus formation and redifferentiation were successfully conducted with elite varieties, including difficult-to-culture varieties. Furthermore, also in corn, the callus formation of difficult-to-culture variety (B73) was successfully conducted for the first time and the redifferentiation has also become possible. B73 is known to be one of the varieties that are most difficult to get callus formation and redifferentiation. According to the present invention, it made it possible to transform B73. Thus, other difficult-to-culture plants and difficult-to-culture varieties are expected to be similarly transformable according to the present invention.

Furthermore, transformed plants expressing a chimeric protein of a protein encoded by nucleic acid 1) or 2) and a protein of interest were successfully obtained.

By means of the above method for improving the transformation efficiency of the nucleic acid molecule into the target plant, the transformation efficiency when the TaWox5 and other nucleic acid molecules are mixed and introduced into the target plant the transformation efficiency is higher than the transformation efficiency when other nucleic acid molecules are introduced into the target plant alone.

According to the present invention, the wheat TaWox5 gene is cloned, and the result of introducing the gene into different wheat shows that the gene can greatly improve the transformation efficiency of wheat. Therefore, not only is the transformation efficiency of easy-to-transform wheat varieties such as Fielder improved, but also the transformation efficiency of difficult-to-transform wheat varieties such as Jimai 22, Aikang 58 and Jing 411 is greatly improved, and the problem of genotype limitation in wheat transformation is solved.

DESCRIPTION OF EMBODIMENTS

Figure 1:
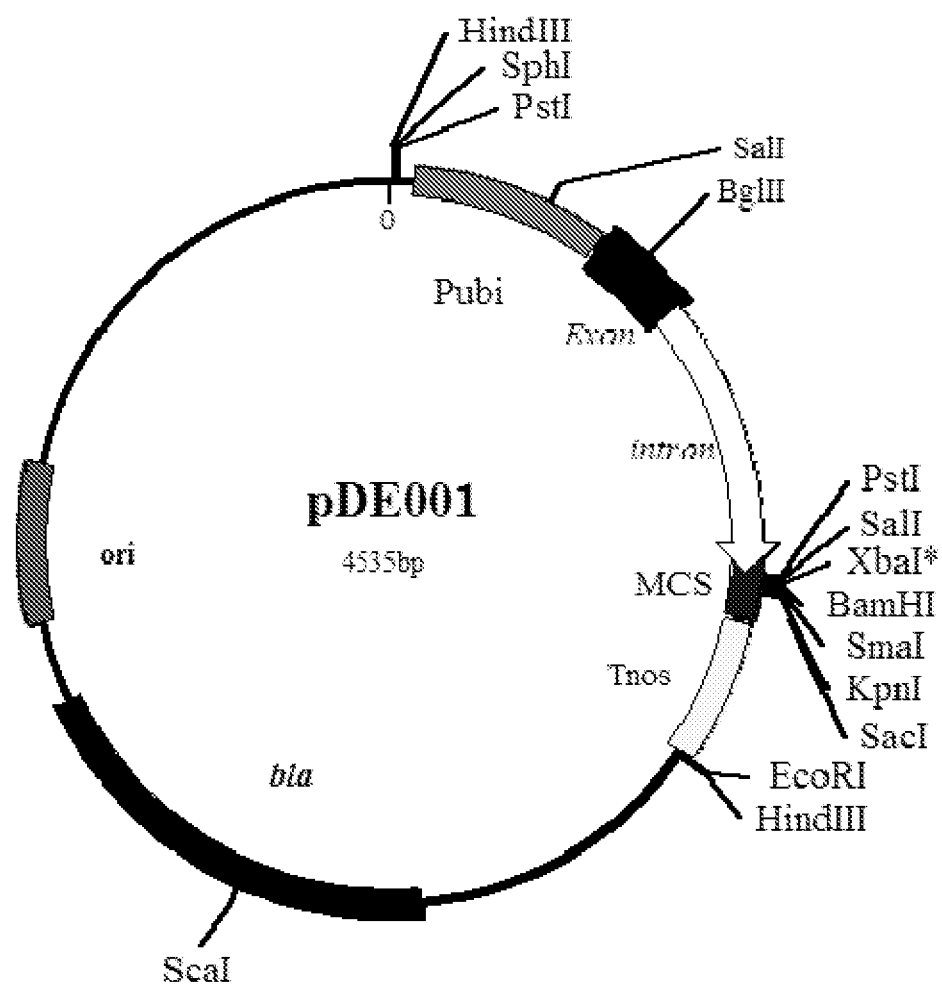
FIG. 1 is a schematic diagram of a pDE001 vector.

1. Method for Improving Transformation Efficiency of Plant

In one aspect, the present invention relates to a method for improving transformation efficiency of a plant.

Without limiting, the method for improving transformation efficiency of a plant comprises making overexpressed in the plant.

1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or 2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant.

(1) Nucleic Acid

The nucleic acid according to the present invention is
1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or 2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant.

The amino acid sequence set forth in SEQ ID NO: 2 is an amino acid sequence encoded by a WOX5-related gene (TaWox5 gene) derived from wheat found in the present invention. The WOX-related gene (TaWox5 gene) derived from wheat has the amino acid sequence set forth in SEQ ID NO: 2. The amino acid sequence set forth in SEQ ID NO: 2 is encoded by the nucleic acid sequence set forth in SEQ ID NO: 11 (cDNA sequence) corresponding to the nucleotides 11825 to 12573 of the nucleic acid sequence set forth in SEQ ID NO: 1 (genome DNA sequence).

The amino acid sequence set forth in SEQ ID NO: 4 is an amino acid sequence encoded by a WOX5-related gene (OsWox5 gene) derived from rice. The WOX5-related gene derived from rice has an amino acid sequence of SEQ ID NO: 4. The amino acid sequence of SEQ ID NO: 4 is encoded by the nucleic acid sequence set forth in SEQ ID NO: 12 (cDNA sequence) corresponding to the nucleic acid sequence set forth in SEQ ID NO: 3 (genome DNA sequence).

Nucleic acid 1) is a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant. Nucleic acid 2) is a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant.

The amino acid sequence encoded by nucleic acid 1) or nucleic acid 2) includes a variant of the amino acid sequence set forth in SEQ ID NO: 2 or SEQ ID NO: 4 and, more specifically, amino acid sequences having at least 85%, 86%, 87%, 88%, 89%, 90%, 91%, 92%, 93%, 94%, 95%, 96%, 97%, 98%, 99%, 99.5% identity with the amino acid sequence set forth in SEQ ID NO: 2 or SEQ ID NO: 4. In one aspect, the amino acid sequence encoded by nucleic acid 1) or nucleic acid 2) according to the present invention includes an amino acid sequence having at least 95% identity with the amino acid sequence set forth in SEQ ID NO: 2 or SEQ ID NO: 4.

As used herein, % of identity between 2 amino acid sequences can be determined by visual inspection and a mathematical calculation. Moreover, % of identity can be determined using a computer program. Examples of such a computer program include BLAST and ClustalW. In particular, the conditions (parameters) for the identity search by the BLAST program are as described in Altschul et al. (Nucl. Acids. Res., 25, p.3389-3402, 1997) and are publicly available from the websites of NCBI and DNA Data Bank of Japan (DDBJ) (BLAST manual, Altschul et al. NCB/NLM/NIH Bethesda, Md. 20894; Altschul et al). Moreover, % of identity can be determined using a program such as genetic information processing software GENETYX Ver.7 (GENETYX), DNASIS Pro (Hitachi Software Engineering Co., Ltd.), or Vector NTI (Infomax).

Nucleic acid 1) or nucleic acid 2) may be the nucleotides nucleic acid sequence set forth in SEQ ID NO: 11, or a variant of the nucleic acid sequence set forth in SEQ ID NO: 12.

Specifically, the nucleic acid may be, for example, a nucleic acid sequence modified from the nucleic acid sequence set forth in SEQ ID NO: 11 or the nucleic acid sequence set forth in SEQ ID NO: 12 by "deletion, substitution, insertion, or addition of 1 or more nucleotides".

As used herein, "deletion, substitution, insertion, or addition of 1 or several nucleotides" regarding a nucleic acid sequence refers to a nucleic acid sequence in which 1 or several nucleotides are deleted or substituted with other nucleotides, other nucleotides are inserted, and/or other nucleotides are added in comparison with a target nucleic acid sequence. The "several nucleotides" means, without limiting, 600 or less, 300 or less, 150 or less, 100 or less, 50 or less, 30 or less, 20 or less, 15 or less, 12 or less, 10 or less, 8 or less, 6 or less, 4 or less, 3 or less nucleotides. Alternatively, the term "several nucleotides" means nucleotides that is 30%, preferably 25%, 20%, 15%, 10%, 5%, 3%, 2%, or 1% of the full length of the nucleic acid sequence. It is preferred that no frameshift occurs in the sequence encoding amino acids by the aforementioned deletion, substitution, insertion, or addition of nucleotides.

Alternatively, nucleic acid 1) or nucleic acid 2) comprises the nucleotides 11825 to 12573 of the nucleic acid sequence set forth in SEQ ID NO: 1 or a nucleic acid sequence having at least 85%, 86%, 87%, 88%, 89%, 90%, 91%, 92%, 93%, 94%, 95%, 96%, 97%, 98%, 99%, 99.5% identity with the nucleic acid sequence set forth in SEQ ID NO 3 or consists of any of these nucleic acid sequences. In one aspect, nucleic acid 1) or nucleic acid 2) according to the present invention comprises a nucleic acid sequence having at least 95% identity with the nucleic acid sequence set forth in SEQ ID NO: 11 or the nucleic acid sequence set forth in SEQ ID NO: 12.

As used herein, % of identity between 2 amino acid sequences can be determined by visual inspection and a mathematical calculation. Moreover, % of identity can be determined using a computer program. Examples of such a sequence comparison computer program include BLASTN program (Altschul et al. (1990), J. Mol. Biol., 215:403-10), version 2.2.7 or WU-BLAST 2.0 algorithm, available from the website of the American national medical library: https://blast.ncbi.nlm.nih.gov/Blast.cgi. The setting of standard default parameters for WU-BLAST 2.0 described in the internet site: http://blast.wustl.edu can be used.

Alternatively, nucleic acid 1) or nucleic acid 2) may be a nucleic acid that hybridizes with the nucleic acid sequence set forth in SEQ ID NO: 11 or the nucleic acid sequence set forth in SEQ ID NO: 12 under stringent conditions. Alternatively, nucleic acid 1) or nucleic acid 2) may be a nucleic acid that hybridizes with a nucleic acid complementary to the nucleic acid sequence set forth in SEQ ID NO: 11 or the nucleic acid sequence set forth in SEQ ID NO: 12 under stringent conditions.

The term "under stringent conditions" as used herein means hybridization in moderately or highly stringent conditions. Specifically, the moderately stringent conditions can easily be determined by a person of ordinary skill, for example, based on the length of DNA. The basic conditions are illustrated in Sambrook et al, Molecular Cloning: A Laboratory Manual, third edition, Chapter 6-7, Cold Spring Harbor Laboratory Press, 2001. Preferably, examples of the moderately stringent conditions include hybridization conditions that are 1×SSC to 6×SSC and 42° C. to 55° C., more preferably conditions that are 1×SSC to 3×SSC and 45° C. to 50° C., and most preferably conditions that are 2×SSC and 50° C. If the hybridization solution contains, for example, approximately 50% of formamide, then a temperature that is 5 to 15° C. lower than the temperatures described above will be used. Examples of washing conditions include 0.5×SSC to 6×SSC at 40° C. to 60° C. In hybridization and washing, generally 0.05% to 0.2%, preferably approximately 0.1% of SDS may be added. The highly stringent conditions can easily be determined by a person skilled in the art, for example, based on the length of DNA. In general, the highly stringent (high-stringent) conditions include hybridization and/or washing at a temperature higher and/or a lower salt concentration than those of moderately stringent conditions. Examples of the conditions include hybridization conditions that are 0.1×SSC to 2×SSC and 55° C. to 65° C., more preferably conditions that are 0.1×SSC to 1×SSC and 60° C. to 65° C., and most preferably conditions that are 0.2×SSC and 63° C. Examples of the washing conditions include conditions that are 0.2×SSC to 2×SSC and 50° C. to 68° C. and more preferably 0.2×SSC and 60 to 65° C.

Nucleic acid 1) and nucleic acid 2) encode polypeptides having a function that improves transformation efficiency of a plant. Nucleic acid 1) and nucleic acid 2) are WOX5-related genes. In one aspect, nucleic acid 1) and nucleic acid 2) maintain functions that WOX5-related genes have (including functions of proteins encoded by WOX5-related genes). An example of the functions encoded by WOX5-related genes is maintenance of stem cells.

Identity between the amino acid sequences of SEQ ID NO: 2 and SEQ ID NO: 4 is 79%. Identity of the nucleic acid sequence set forth in SEQ ID NO: 11 and the nucleic acid sequences set forth in SEQ ID NO: 12 is 84%.

(2) Plant

In the present invention, the kind of the plant whose transformation efficiency is to be improved is not particularly limited.

The plant may be either a dicotyledon or a monocotyledon and it is preferably a monocotyledon. Further preferably, it is a plant in the family Poaceae, more preferably it is corn, wheat, barley, rice, sorghum, rye, or the like, and most preferably it is corn, wheat, or rice.

The method according to the present invention can be used for a plant or a variety considered to be "difficult-to-culture" in particular, but without limiting. The term "difficult-to-culture" means that it is difficult to culture and more specifically that it is difficult, for example, to culture cells isolated from the plant body, to form callus by treatment such as dedifferentiation, or to redifferentiate callus into plant bodies.

In general, monocotyledons are more difficult to culture than dicotyledons, but examples of the "difficult-to-culture" plants include soybean, kidney bean, and red pepper. The term "difficult-to-culture varieties" means varieties that are difficult to culture than general research varieties (such as A188 for corn) of the same species. Examples thereof include corn B73 or elite corn varieties derived from B73; elite wheat varieties (e.g., TAM); barley varieties other than Golden Promise and Igri; and sorghum varieties other than 296B, C401, SA281, P898012, Pioneer 8505, and Tx430.

(3) Overexpression

In the present invention, a gene is made overexpressed in a plant.

The term "make (a nucleic acid) overexpressed" (herein, also simply referred to as "express") refers to artificially expressing a nucleic acid that is not expressed in natural conditions or artificially expressing a nucleic acid at an amount more than that expressed in natural conditions.

The means for overexpressing the nucleic acid is not particularly limited. Any known means that allows overexpression of a nucleic acid in plants (including any form such as ova, sperm, seeds, cells, immature embryos, mature embryos, callus, and adult plants) may be used. A gene can be introduced into a plant by a gene transfer technique such as, but not particularly limited to, Agrobacterium-mediated gene transfer after incorporating a foreign gene into a vector. Moreover, a gene present in a plant may be overexpressed using a technique such as the genome editing.

The method of gene transfer for introducing an exogenous nucleic acid is not particularly limited and examples thereof include know methods such as Agrobacterium-mediated gene transfer, polyethyleneglycol (PEG) method, whisker method, microinjection, glass beads method, particle bombardment, and electroporation.

The technique of the genome editing for overexpressing a gene present in a plant is not particularly limited. Examples thereof include the CRISPR-Cas method, the TALLEN method, zinc finger-mediated mutagenesis, chilling, homologous recombination, oligonucleotide-specific mutagenesis, mega nuclease-mediated mutagenesis and a combination thereof. Examples of methods include, without limiting, methods for editing the promoter of an endogenous gene to overexpress the gene and methods for editing a part of an endogenous gene to change it into a gene sequences according to the present invention.

In one aspect, the overexpression includes not only constitutive overexpression of the aforementioned nucleic acid, but also transient or site-specific overexpression.

(4) Transformation Efficiency

The method according to the present invention improves the transformation efficiency of a plant. The term "improve the transformation efficiency" generally refers to one or more of a) improvement of efficiency of callus formation of the plant; b) improvement of redifferentiation rate of the plant; and c) improvement of gene transfer efficiency. To "improve transformation efficiency" is preferably improvement of efficiency of callus formation and/or improvement of redifferentiation rate and further preferably improvement of efficiency of callus formation.

The term "improve" refers to; without limiting, improving the efficiency of callus formation of the plant, the redifferentiation rate of the plant, or the gene transfer efficiency, for example, 1.5 or more times, 2 or more times, 3 or more times, 4 or more times, or 5 or more times in comparison with that when the aforementioned nucleic acid is not overexpressed. Alternatively, it refers to making the callus formation of the plant, the redifferentiation of the plant, or the gene transfer possible when it is not possible without the overexpression of the aforementioned nucleic acid.

For example, in Examples described herein below, both the efficiency of callus formation and the efficiency of redifferentiation were improved only by the overexpression of the aforementioned nucleic acid in wheat. Furthermore, the callus formation of corn, which was impossible before the present invention, has become possible.

2. Nucleic Acid Construct (Embodiment A)

In one aspect, the present invention relates to a nucleic acid construct (embodiment A).

Without limiting, the nucleic acid construct (embodiment A) comprises 1) a nucleic acid encoding the amino acid sequence set forth in SEQ ID NO: 2 or a nucleic acid encoding a polypeptide comprising an amino acid sequence having an at least 85% identity with the amino acid sequence set forth in SEQ ID NO: 2 and having a function that improves transformation efficiency of a plant; or 2) a nucleic acid encoding the amino acid sequence set forth in SEQ ID NO: 4 or a nucleic acid encoding a polypeptide comprising an amino acid sequence having an at least 85% identity with the amino acid sequence set forth in SEQ ID NO: 4 and having a function that improves transformation efficiency of a plant;

and a promoter for producing a nucleic acid in the plant.

Nucleic acid 1) or 2) is as described in "1. Method for improving transformation efficiency of plant" above.

(1) Promoter

The nucleic acid construct of the present invention includes a promoter for expressing the nucleic acid in a target plant.

The promoter is not particularly limited as long as the promoter can achieve a transcription of a nucleic acid of interest in a target plant cell. In one embodiment, the promoter is a constitutive promoter, an inducible promoter, or a site-specific promoter.

Examples of the promoter include cauliflower mosaic virus 35S promoter (CaMV35S), various ubiquitin promoters, various actin promoters, tobacco PR1a gene promoter, nopaline synthase gene promoter, napin gene promoter, oleosin gene promoter, and the like.

In one embodiment, an inducible promoter may be used. Examples of the inducible promoter include a promoter known that whose expression is induced by external factors, such as infection or invasion of filamentous fungi, bacteria, or viruses; low temperature, high temperature, drying, or irradiation with ultraviolet rays; application of specific chemicals, such as hormone like auxin and brassinosteroid; and other external factors. More specific examples of the promoter include the promoter of rice chitinase gene (Xu et al. 1996 Plant Mol. Biol. 30: 387) and the promoter of PR protein genes of tobacco (Ohshima et al. 1990 Plant Cell 2: 95) whose expressions are induced by infection or invasion of filamentous fungi, bacteria, or viruses; the promoter of rice "lip19" gene (Aguan et al. 1993 Mol. Gen. Genet. 240:1) whose expression is induced by low temperature; the promoters of rice "hsp80" gene and "hsp72" gene (Van Breusegem et al. 1994 Planta 193:57) whose expressions are induced by high temperature; the promoter of Aarabidopsis thaliana "rab16" gene (Nundy et al. 1990 Proc. Natl. Acad. Sci. USA 87:1406) whose expression is induced by drying; the promoter of parsley chalcone synthase gene (Schulze-Lefert et al. 1989 EMBO J. 8:651) whose expression is induced by irradiation with ultraviolet rays; the promoter of maize alcohol dehydrogenase gene (Walker et al. 1987 Proc. Natl. Acad. Sci. USA 84:6624) whose expression is induced by anaerobic conditions; and the promoter whose expression is induced by salt stress (Shinozaki, K. and Yamaguchi-Shinozaki, K., Curr. Opin. Plant Biol. 3, 217-223 (2000)). Moreover, the tetracycline-inducible system using the tetracycline resistance operon (tet operon) existing in transposon Tn10 of E. coli induced by tetracycline; the amino acid sequence of LexA (amino acids 1-87), a repressor of the SOS regulon of E. coli induced by estradiol; the transcriptional active site (amino acid residues 403-479) of VP16 (amino acid sequence) from Herpes Simplex Virus (HSV); the synthetic transcriptional activator XVE (amino acid sequence) prepared by fusing the regulatory region of the human estrogen receptor (amino acid residues 282-595); and the transcriptional induction system in which a plurality of SOS boxes (5'-TACTGTATATATATACAGTA-3'), originally an operator that LexA binds to, are arranged in upstream of TATA box of CaMV 35S minimal promoter as cis sequences that XVE binds to.

A site-specific promoter may also be used. Examples of the site-specific promoter include leaf-specific promoter for expressing a nucleic acid (e.g., rice psb0 gene promoter (JP-A-2010-166924)), stem-specific promoter for expressing a nucleic acid (for example, Arabidopsis thaliana FA6 promoter (Gupta et al. 2012 Plant Cell Rep 31: 839-850), root specific promoter for expressing a nucleic acid (for example, RCc3 promoter (Xu et al. 1995 Plant Mol Biol 27: 237-248), and promoters that express mainly in vegetative organs of roots, stems and leaves (for example, Arabidopsis thaliana AS promoter).

In one embodiment of the present invention, simply by overexpres sing the nucleic acid, it is possible to form a callus of the target plant which had difficulty in forming callus, and to improve transformation efficiency. Without limitation, in one embodiment, the promoter is not an inducible promoter, but a constitutive promoter.

(2) Vector

The nucleic acid of 1) or 2) and the promoter for expressing the nucleic acid in a target plant may be linked to any vector. A "vector" is a nucleic acid molecule for amplifying, maintaining and introducing a recombinant nucleic acid to be used in gene recombinant technology. The vector containing a nucleic acid and a promoter for expressing the nucleic acid in a target plant as a whole may be referred to as a nucleic acid construct or a vector. Note that the vector may be linear or circular, and preferably circular.

An available vector for recombination may be used to ligate the nucleic acid and the promoter for expressing the nucleic acid in a target plant in a conventional manner. The vector used in the present invention is not particularly limited as long as it can be used to achieve the aimed effects of the present invention in a target plant cell. For example, vectors of pBI series, vectors of pBluescript series and vectors of pUC series may be used. Examples of the pBI series vectors include pBI121, pBI101, pBI101.2, pBI101.3, and pBI221. Binary vectors such as the pBI series vectors are preferred in that they can introduce a nucleic acid of interest via Agrobacterium into a target plant. Examples of the pBluescript series vectors include pBluescript SK(+), pBluescript SK(−), pBluescript II KS(+), pBluescript II KS(−), pBluescript II SK(+), and pBluescript II SK(−). Examples of the pUC series vectors include pUC19 and pUC119. The pBluescript series and pUC series vectors are preferred in that they can directly introduce a nucleic acid into a target plant. Furthermore, binary vectors such as pGreen series (www.pgreen.ac.uk), pCAMBIA series (www.cambia.org) and pLC series (WO2007/148819) vectors, and super-binary vectors such as pSB11 (Komari et al, 1996, Plant J, 10: 165-174) and pSB200 (Komori et al, 2004, Plant J, 37: 315-325) vectors can also be preferably used. In addition, vectors made by combining these parts can also be preferably used.

The vector of the present invention may further contain a transformant identification marker. As the marker, for example, a drug-selectable marker gene can be used. The drug-selectable marker gene is not particularly limited, and any known gene can be used. Specific examples of the drug-selectable marker gene include gentamicin resistance gene, kanamycin resistance gene, ampicillin resistance gene, spectinomycin resistance gene, tetracycline resistance gene, hygromycin resistance gene and a number of other drug-selectable marker genes. Further, a phosphinothricin acetyltransferase gene (bar) resistant to the herbicide phosphinothricin and the like may be used. Furthermore, a marker gene labeled with a fluorescent material, such as DsRed2 (TaKaRa-Bio) and GFP, can be used.

The vector of the present invention may further contain a transcription terminator sequence and the like. The transcription terminator sequence is not particularly limited as long as it has a function as a transcription termination site, and may be any known transcription terminator sequence. The transcription terminator sequence is selectable depending on the promoter used, and examples thereof include a transcription termination region of cauliflower mosaic virus 35S (CaMV35S terminator) and a transcription termination region of nopaline synthase gene (Nos terminator). In the recombinant expression vector described above, by arranging the transcription terminator sequence in an appropriate place, it is possible to prevent the occurrence of phenomena such as the synthesis of unnecessarily long transcripts, after the vector is introduced into a target plant cell. Further, the recombinant expression vector may further contain other nucleic acid segments. The other nucleic acid segment is not particularly limited, and examples thereof include a transformant selection marker, an enhancer, and a nucleotide sequence for enhancing translation efficiency. Further, the recombinant expression vector described above may further include a T-DNA region. The T-DNA region, especially when the recombinant expression vector is introduced into a target plant using *Agrobacterium*, can enhance the efficiency of gene transfer. Note that the number of T-DNA per recombinant expression vector is not determined, and it can be selected according to the purpose.

Examples of the nucleotide sequence for enhancing translation efficiency include an omega sequence from tobacco mosaic virus. By arranging the omega sequence in the untranslated region of the promoter (5'UTR), it is possible to enhance the translation efficiency of the fusion gene.

Further, examples of the enhancer include an enhancer region containing a sequence of the upstream side within CaMV35S promoter. Thus, the recombinant expression vector described above can include various nucleic acid segments depending on the purpose.

The nucleic acid construct of the present invention (embodiment A) may be used in a method for improving the transformation efficiency in a target plant and/or a transforming method of a target plant of the present invention. The present invention includes the use of the nucleic acid construct in the method for improving the transformation efficiency in a target plant and the use of the nucleic acid construct in the transforming method.

3. Transforming Method (Embodiment A)

In one embodiment, the present invention includes a transforming method of a target plant (embodiment A).

The transforming method of a target plant (embodiment A) includes introducing the nucleic acid construct (embodiment A) and a desired nucleic acid to be expressed in a target plant into the target plant.

The "desired nucleic acid to be expressed in a target plant" (Gene of interest: GOI) is a nucleic acid having any of the sequences to be introduced into a target plant cell, and not particularly limited. It may be a nucleic acid sequence encoding an amino acid sequence (structural gene) or may be a non-structural gene. The nucleic acid sequence of interest may be linked to a desired promoter and a terminator. For example, it may be a set of a gene capable of obtaining a desired trait (phenotype) by overexpressing in a target plant and a promoter, and may be, like RNAi, a nucleic acid sequence capable of obtaining a desired trait by suppressing a plant endogenous gene. Furthermore, it may be a nucleic acid sequence for performing genome editing, like a gene encoding Cas protein and a guide sequence.

The length of the nucleic acid is not particularly limited, but preferably is a length suitable for being introduced into a target plant cell with the nucleic acid construct (embodiment A) and expressed. Without limitation, the length is 100 kbp or less, preferably 50 kbp or less, more preferably 30 kbp, 10 kbp or less, and 1 kbp or less.

The means for introducing the nucleic acid construct (embodiment A) and the desired nucleic acid to be expressed in a target plant into the target plant is not particularly limited. Without limitation, the means may include incorporating a foreign gene into a vector or the like, and then introducing the gene into a target plant by a gene transfer method such as *Agrobacterium* method. Alternatively, the means for introducing the nucleic acid construct (embodiment A) and the desired nucleic acid to be expressed in a target plant into the target plant may include the embodiment in which a gene present in a target plant is edited by using the technique of genomic editing or the like and expressed.

The order of introduction is not limited as long as both the nucleic acid construct (embodiment A) and the desired nucleic acid to be expressed in a target plant have been introduced at certain point in the process of transforming the target plant. The nucleic acid construct and the desired nucleic acid to be expressed in a target plant may be introduced simultaneously (co-transformation), or a transformed plant obtained by introducing the nucleic acid construct may be previously generated and then the desired nucleic acid to be expressed in the target plant be introduced into the generated transformed plant, or vice versa.

The nucleic acid construct and the desired nucleic acid to be expressed in a target plant may be present in different vectors, or may be present in one vector. When both present in one vector, they may be under control of the same promoter, or may be under control of different promoters. The nucleic acid construct and the desired nucleic acid to be expressed in a target plant may be introduced into the target plant while remaining on the linear fragment, and then be expressed.

Co-transformation is to transform two or more independent exogenous genetic materials at the same time. Examples of the co-transformation method include a method for introducing a plurality of binary vector each having a plurality of T-DNA during a single gene transfer into a target plant (multi-vector method), a method for introducing one binary vector having two or more T-DNA during a single gene transfer (one-vector, multi-T-DNA method), a method for introducing one binary vector having only one T-DNA during a single gene transfer and arranging one T-DNA which constitutes two or more genes by using two or more right border sequences (one vector, two border method: Yau and Stewart, 2013); and a method for introducing one binary vector having only one T-DNA, the T-DNA having two or more promoters, desired nucleic acids to be expressed in a target plant, and terminators during a single gene transfer (one vector, one T-DNA method). In the present invention, any of these means can be preferably performed.

The type of the vector for introducing the nucleic acid construct and the desired nucleic acid to be expressed in a target plant is not particularly limited. Any vector as described in "2. nucleic acid construct (embodiment A)" can be used. In the case of multi-vector method, the vector may be used in any combination.

Furthermore, the nucleic acid construct and/or the desired nucleic acid to be expressed in a target plant may be transiently expressed or stably expressed. In one embodiment, without limitation, the nucleic acid construct or the desired nucleic acid to be expressed in a target plant is transiently expressed.

4. Transformed Plant (Embodiment A)

In one embodiment, the invention relates to the transformed plant (embodiment A).

The transformed plant of the present invention (embodiment A) is a transformed plant obtained by the transforming method of the present invention (embodiment A). Especially, the present invention has enabled for the first time to provide a transformed plant in so-called "difficult-to-culture" plant or varieties. In the transformed plant of the present invention, the nucleic acid is constitutively, transiently, or site-specifically overexpressed.

5. Nucleic Acid Construct (Embodiment B)

In one embodiment, the present invention relates to a nucleic acid construct (embodiment B).

Without limitation, the nucleic acid construct (embodiment B) includes 1) a nucleic acid encoding the amino acid sequence of SEQ ID NO: 2, or a nucleic acid encoding a polypeptide having an amino acid sequence having at least 85% identity to the amino acid sequence of SEQ ID NO: 2 and having the function of improving the transformation efficiency in a target plant; or 2) a nucleic acid encoding the amino acid sequence of SEQ ID NO: 4, or a nucleic acid encoding a polypeptide having an amino acid sequence having at least 85% identity to the amino acid sequence of SEQ ID NO: 4 and having the function of improving the transformation efficiency in a target plant, a promoter for expressing the nucleic acid in a target plant, and a desired nucleic acid to be expressed in the target plant.

The nucleic acid of 1) or 2) is as described above in "1. Method For Improving Transformation Efficiency in Target Plant". The promoter for expressing the nucleic acid in a target plant is as described above in "2. Nucleic Acid Construct (Embodiment A)". The desired nucleic acid to be expressed in a target plant is as described above in "3. Transforming Method (embodiment A)".

The nucleic acid of 1) or 2) and the promoter for expressing the nucleic acid in a target plant may be linked to any vector. "Vector" is as described above in "2. Nucleic Acid Construct (Embodiment A)".

By the expression of the nucleic acid construct (embodiment B) in a target plant, a fusion protein composed of the protein encoded by the nucleic acid of 1) or 2) and the protein encoded by the desired nucleic acid, i.e., the chimeric protein, is obtained. The method for preparing the chimeric protein is not particularly limited, and any known genetic engineering technique may be used to express the chimeric protein.

Without limitation, in one embodiment, the nucleic acid of 1) or 2) and the desired nucleic acid to be expressed in a target plant is ligated directly or via a linker. In one embodiment, the desired nucleic acid to be expressed in a target plant is ligated to the 3'-side of the nucleic acid of 1) or 2).

In the chimeric protein obtainable by the expression of the nucleic acid construct (embodiment B) in a target plant, the protein encoded by the nucleic acid of 1) or 2) and the protein encoded by the desired nucleic acid may be bonded directly or via a linker. The linker is not particularly limited and may be an amino acid linker. In one embodiment, the length of amino acid linker is, without limitation, 1 amino acid residue or more, two amino acid residues or more, 3 amino acid residues or more, 4 amino acid residues or more, 5 amino acid residues or more, 8 amino acid residues or more, 10 amino acid residues or more, and 12 amino acid residues or more. In one embodiment, the length of amino acid linker is, without limitation, 50 amino acid residues or less, 40 amino acid residues or less, 30 amino acid residues or less, 25 amino acid residues or less, 20 amino acid residues or less, 15 amino acid residues or less, and 12 amino acid residues or less. In one embodiment, the length of amino acid linker is, without limitation, in the range of 1-50 amino acid residues, preferably 5-25 amino acid residues. It is preferable that the linker does not affect the functions of the protein encoded by the nucleic acid of 1) or 2) and of the protein encoded by the desired nucleic acid, and for example, the neutral amino acids such as glycine, serine, or alanine are preferable.

In the chimeric protein, the protein encoded by the nucleic acid of 1) or 2) may be bonded to either the N-terminal side or C-terminal side of the protein encoded by the desired nucleic acid. Preferably, the protein encoded by the nucleic acid of 1) or 2) is at the N-terminal side of the protein encoded by the desired nucleic acid. In Example 5, a higher transformation efficiency was obtained when the protein encoded by the nucleic acid of 1) or 2) was at the N-terminal side.

The nucleic acid construct of the present invention (embodiment B) may be used in a method for improving the transformation efficiency in a target plant and/or a transforming method of a target plant of the present invention. The present invention includes the use of the nucleic acid construct in a method for improving the transformation efficiency in a target plant and the use of the nucleic acid construct in a transforming method.

6. Transforming Method (Embodiment B)

In one embodiment, the present invention includes a transforming method of a target plant (embodiment B).

The transforming method of the present invention (embodiment B) includes introducing the nucleic acid construct (embodiment B) into a target plant.

The nucleic acid construct (embodiment B) is as described in "5. Nucleic Acid Construct (embodiment B)". The means for introducing a nucleic acid construct (embodiment B) in a target plant is not particularly limited and as described in "3. Transforming Method (embodiment A)". By performing the transforming method of a target plant (embodiment B) in the target plant, a fusion protein composed of the proteins encoded by the nucleic acid of 1) or 2) and the protein encoded by the desired nucleic acid, i.e., the chimeric protein is expressed in the target plant.

Without limitation, in one embodiment, the nucleic acid construct (embodiment B) is transiently expressed.

7. Transformed Plant (Embodiment B)

In one embodiment, the present invention relates to the transformed plant (embodiment B).

The transformed plant of the present invention (embodiment B) is a transformed plant obtained by the transforming method of the present invention (embodiment B). The present invention has especially enabled for the first time to provide a transformed plant in so-called "difficult-to-culture" plant or varieties. In the transformed plant of the present invention (embodiment B), the chimeric protein of the protein encoded by the nucleic acid of 1) or 2) and the protein encoded by the desired nucleic acid is constitutively, transiently, or site-specifically overexpressed.

EXAMPLES

Hereinafter, the present invention will be described in detail with reference to examples, but the present invention is not limited to these examples. Those skilled in the art can readily add modifications and/or changes to the present invention based on the description herein, and those modified and/or changed inventions are also included in the technical scope of the present invention.

The experimental methods used in the following examples are conventional methods, unless otherwise specified.

The materials, reagents and the like used in the following examples are commercially available, unless otherwise specified.

Plasmids and strains illustrated in the examples below are for the purpose of further elaboration of the present invention and are not intended to limit the substantial content of the present invention. Where specific test conditions are not indicated, they are the conventional conditions well-known to those skilled in the art, such as those described by Sambrook, et al, in molecular cloning: the experimental manual (New York: Cold Spring Harbor Laboratory Press, 1989), or those suggested by the manufacturer.

Example 1

The plasmids and strains illustrated in this example are derived from the followings:

a cloning vector pMD-18T is a commercially available product of Takara;

plant expression vectors pDE001 and pDE003 are commercially available products of Biodee;

*Escherichia coli* TOP 10 is a commercially available product of Beijing TransGen Biotech; *Escherichia coli* PRK2013 and *Agrobacterium tumefaciens* C58C1 are preserved by the present laboratory.

Kenong 199, Lunxuan 987, Jimai 22, Aikang 58, Yangmai 16, Jing 411, Fielder, CB037 and Xinong 979 are all recorded in the following literatures: Wang et. al., 2017 Generation of marker-free transgenic hexaploid wheat via an *Agrobacterium*-mediated co-transformation strategy in commercial Chinese wheat varieties Plant biotechnology journal 15:614-623; Rongcheng Wang, Rui Zhang, Effect of Fertilizer Application on Yield and Population of Strong Gluten Wheat Xinong 979, Acta Agriculturae Boreali-occidentalis Sinica, 2012, 21 (6): 63-66.

This examples describes Wheat TaWox5 Gene Cloning and Its Application in Wheat Transgene.

I. Wheat TaWox5 Gene Cloning

Design primers (F: GTGTCAATGGAGGCGCTGAGCG; R:GTGTCAATGGAGGCGCTGAGCG)).(SEQ ID NO: 5 and SEQ ID NO: 6)

A genomic DNA of a wheat strain CB037 is extracted as a template and subject to AS-PCR amplification using the primers F and R described above to obtain about 760 bp fragments.

The PCR product is connected to a pMD-18T vector to obtain pMD-18T-TaWox5, and sent for sequencing.

The sequencing result is that the PCR product has nucleotide shown in SEQ ID NO: 1 in a sequence table, named an TaWox5 Gene. The gene is 749 bp in length, contains a 116 bp intron and encodes 210 amino acids. The amino acid sequence of a protein coded by the gene is SEQ ID NO: 2, which is named TaWox5.

The SEQ ID NO: 1 may also be synthesized artificially and connected to a pMD-18T vector to obtain pMD-18T-TaWox5.

II. Application of Wheat TaWox5 Gene in Wheat Transgene

1. Construction of Plant Transformation Vector pDE003-TaWox5

Figure 2:
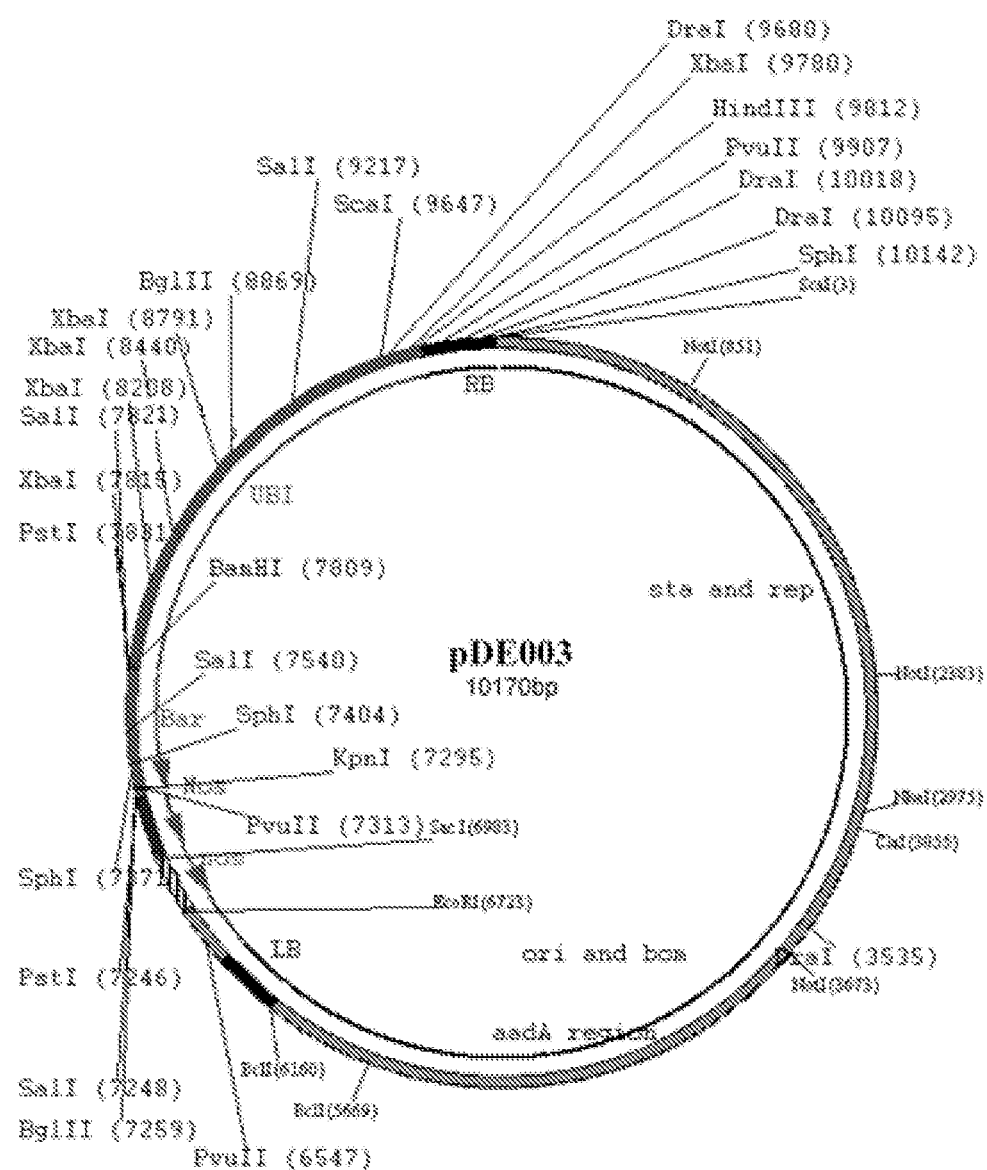
FIG. 2 is a schematic diagram of a pDE003 vector.
Figure 3:
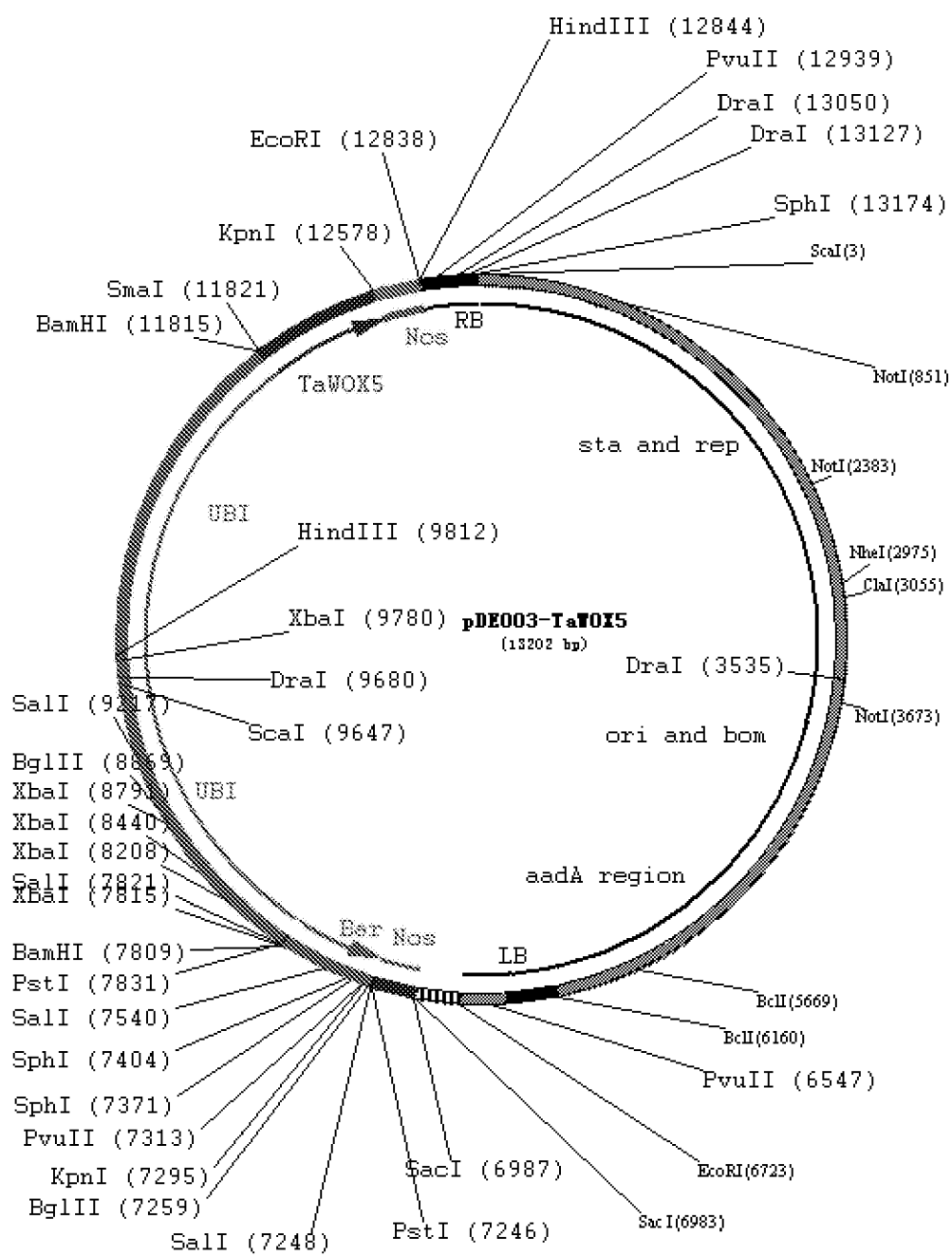
FIG. 3 is a schematic diagram of a pDE003-TaWox5 vector.

The primers Wox5SmaF: AAACCCGGGATGGAGGCGCTGAGCGG and Wox5KpnR: AAAGGTACCTTAGACCAGATACCGAT (SEQ ID No: 7 and 8), respectively and subject to PCR amplification with pMD-18T-TaWox5 as a template using high fidelity enzyme KOD. Then, the PCR product and the pDE001 vector (FIG. 1) are subject to enzyme digestion with KpnI and SmaI to obtain a 773 bp PCR amplification product and a 4535 bp pDE001 vector backbone. Finally, the 773 bp PCR amplification product and the 4535 bp pDE001 vector backbone are connected to obtain an intermediate plant expression vector pDE001-TaWox5. The pDE001-TaWox5 and pDE003 (FIG. 2) are then subject to enzyme digestion with HindIII to obtain a 3033 bp TaWox5 enzyme-digested product and a10170 bp pDE003 vector backbone. Finally, the two enzyme-digested products are connected to obtain a final plant expression vector pDE003-TaWox5 (FIG. 3).

A nucleotide sequence of the pDE003-TaWox5 vector is SEQ ID NO: 1, which is a vector obtained by inserting DNA molecules (an expression cassette containing the TaWox5 gene) shown in 9812-12837 in SEQ ID NO: 1 into HindIII enzyme digestion sites of the pDE003 vector.

In SEQ ID NO: 1, 7832-9817 sites are of a UBI promoter, 7257-7808 sites are of a Bar gene, 6989-7242 sites are of a Nos terminator, 9818-11815 sites are of a UBI promoter, 11825-12573 sites are of an TaWox5 gene, and 12586-12837 sites are of a Nos terminator.

The plant expression vector pDE003-TaWox5 is transferred to *Escherichia coli* Top 10 to obtain an *Escherichia coli* Top 10 strain containing pDE003-TaWox5.

2. Transfer of Recombinant Plasmid pDE003-TaWox5 into *Agrobacterium* C58C1

1) A host *Agrobacterium* C58C1 strain (Wang et. al., 2017 Generation of marker-free transgenic hexaploid wheat via an *Agrobacterium*-mediated co-transformation strategy in commercial Chinese wheat varieties Plant biotechnology journal 15: 614-623) is cultured in a 4 ml test tube containing Rif, Gen LB media at 180 rpm for 40 h at 28° C. to obtain an *Agrobacterium* C58C1 bacterium solution.

An *Escherichia coli* Top 10 strain containing pDE003-TaWox5 and adjuvant bacterium PRK2013 (Wang et. al., 2017 Generation of marker-free transgenic hexaploid wheat via an *Agrobacterium*-mediated co-transformation strategy in commercial Chinese wheat varieties Plant biotechnology journal 15: 614-623) are cultured in a 4 ml test tube containing a Kan LB medium at 225 rpm for 16 h at 37° C. to obtain an *Escherichia coli* Top 10 bacterium solution containing pDE003-TaWox5 and a PRK2013 bacterium solution.

2) 100 μl of *Agrobacterium* C58C1 bacterium solution, the *Escherichia coli* Top 10 bacterium solution containing pDE003-TaWox5 and the PRK2013 bacterium solution are respectively added to a 1.5 ml centrifuge tube and mixed uniformly; only 100 μl of *Agrobacterium* C58C1 bacterium solution and the adjuvant bacterium PRK2013 solution are respectively added into a 1.5 ml centrifuge tube as controls, and centrifuged at 4000 rpm for 3 min to collect thalli.

3) Supernatant is discarded, the remaining supernatant is sucked up with a pipette, and 50 μl of LB medium without antibiotics is added, and the thalli are resuspended.

4) The thalli are added to an LB solid culture medium without antibiotics. Be careful not to shake flat plates, such that the thalli are clustered, then sealed with a sealing film after the flat plates are aired, and cultured at 28° C. for 24 h.

5) A small amount of thalli is extracted from the bacteria cluster with an inoculating needle, streaked on an LB solid medium containing Rif, Gen, Kan and cultured at 28° C. for 48 h, one target bacterium and one control being streaked on each flat plate.

6) Single clones are picked from the trinity hybridized plates, and the positive *Agrobacterium* strains are identified by PCR.

Primers for PCR identification are primers F and R, and as a result a 700 bp positive *Agrobacterium* strain is obtained.

The positive *Agrobacterium* strain is a recombinant bacterium obtained by transferring the recombinant plasmid pDE003-TaWox5 into *Agrobacterium* C58C1, named *Agrobacterium* C58C1 containing pDE003-TaWox5.

The empty vector pDE003 is transferred into *Agrobacterium* C58C1 by the same method to obtain a recombinant bacterium, named *Agrobacterium* C58C1 containing pDE003.

3. *Agrobacterium*-Mediated Transformation of Wheat

Detailed steps and methods refer to Wang et al., 2016 and Ishida et al., 2015, which are specifically as follows.

1) At 4 days before infection, *Agrobacterium* C58C1 containing pDE003-TaWox5 and

*Agrobacterium* C58C1 containing pDE003 are inoculated into a YEP solid medium containing Gent 50 mg $L^{-1}$, Spec 50 mg $L^{-1}$ and Rif 50 mg $L^{-1}$, respectively and resuscitated at 28° C. for 3 days in dark. Single colonies are picked, added in a 10 ml YEP liquid medium containing Gent 50 mg $L^{-1}$, Spec 50 mg $L^{-1}$ and Rif 50 mg $L^{-1}$, and shaken and cultured overnight at 200 rpm at 28° C. in dark.

2) *Agrobacterium thalli* are collected by centrifugation at 3,500 rpm for 10 min at room temperature. The supernatant is discarded. The *Agrobacterium thalli* are resuspended with MS resuspension (1/10 MS basic medium (Beijing Ximeijie Technology Co., Ltd., Item No. M519, glucose 10 g $L^{-1}$) to obtain an *Agrobacterium* C58C1 resuspension containing pDE003-TaWox5 and an *Agrobacterium* C58C1 resuspension containing pDE003.

3) Different varieties of wheat immature embryos (about 14 days after flowering) appropriate in size are selected and equally divided into two parts, which are mixed with the *A* C58C1 resuspension containing pDE003-TaWox5 and the *Agrobacterium* C58C1 resuspension containing pDE003 and infected, then paved on an AS basic co-culture medium (1/10 MS basic medium, glucose 10 g $L^{-1}$, agarose 8 g $L^{-1}$) at 25° C. for 3 days.

4) The co-cultured immature embryos are transferred to a recovery medium WLS-RES (MS basic medium, 2,4-D 0.5 mg $L^{-1}$, picloram 2.2 mg $L^{-1}$, Cb 400 mg $L^{-1}$, Cef 100 mg $L^{-1}$) for 5 days in dark.

5) The immature embryos subject to recovery culture are transferred to a first screening medium WLS-P5 (MS basic medium, 2,4-D 0.5 mg $L^{-1}$, picloram 2.2 mg $L^{-1}$, PPT 5 mg $L^{-1}$, Cb 400 mg $L^{-1}$, Cef 100 mg $L^{-1}$) for 14 days in dark.

6) Then, callus is transferred to a first screening medium WLS-P10 (MS basic medium, 2,4-D 0.5 mg $L^{-1}$, picloram 2.2 mg $L^{-1}$, PPT 10 mg $L^{-1}$, Cb 400 mg $L^{-1}$) and cultured for 21 days in dark.

7) The callus is transferred to a differentiation medium LSZ-P5 (MS medium, PPT 5 mg $L^{-1}$) and cultured for 2 weeks under light.

8) Green shoots of wheat are separated out and placed in a rooting medium MSF-P5 (MS medium, PPT 5 mg $L^{-1}$, IBA 0.5 mg $L^{-1}$) and cultured for 21 days.

9) Seedlings with well-grown roots are transplanted to soil to obtain the trans-pDE003-TaWox5 seedlings and trans-pDE003 seedlings.

4. Identification of Positive Seedlings

1) PCR Method

The trans-pDE003-TaWox5 seedlings are subject to PCR amplification using the Bar (pDE003 vector containing the Bar gene) primers (F: ACCATCGTCAACCACTACATCG;R:GCTGCCAGAA-ACCACGTCATG).

(SEQ ID NO: 9 and SEQ ID NO: 10)

Figure 4:
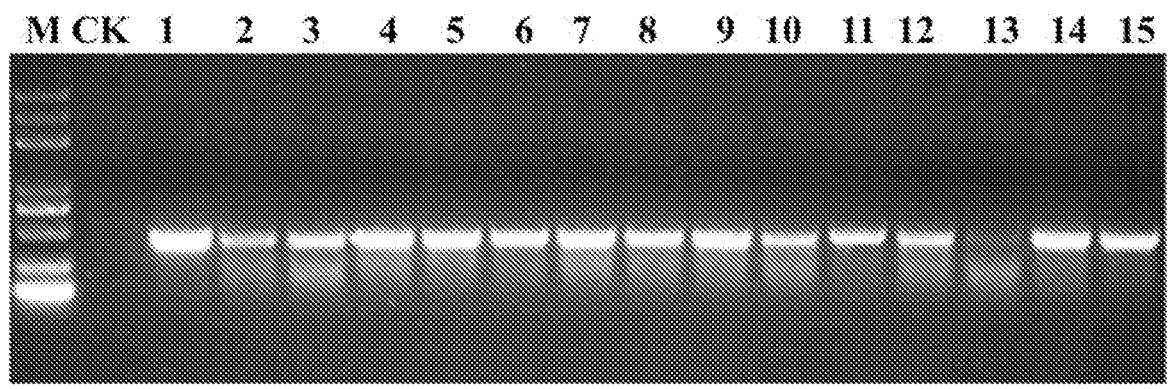
FIG. 4 is a PCR detection result of a Bar gene.

The results are shown in FIG. 4, in which, M: 5000 bp DNA marker; CK: the common wheat Fielder; 1-15: trans-pDE003-TaWox5 seedlings, and it can be seen that 429 bp fragments are positive trans-pDE003-TaWox5 seedlings.

The pDE003 seedlings are subject to PCR amplification, and as a result 429 bp fragments are positive trans-pDE003 seedlings.

The above results indicate that all of the transgenic seedlings are positive.

2) Statistical Analysis on Transformation Efficiency

Transformation efficiency=(positive seedling number/immature embryo number)*%

The results are as shown in Table 1. Compared with the trans-empty vector pDE003, the trans-pDE003-TaWox5 vector can greatly improve the transformation efficiency of wheat of the same variety, for example, the transformation efficiency of the Fielder control is 45.3%, while the transformation efficiency of the trans-TaWox5 vector reaches up to 154%; the transformation efficiency of the Kenong 199 is 22.7%, and the transformation efficiency of the trans-TaWox5 vector is improved to about 70%; the transformation efficiency of the trans-TaWox5 vectors of the varieties having a lower transformation efficiency, such as Jimai 22, Lunxuan 987 and Yangmai 16 is improved to over 20% respectively; in addition, the transformation efficiency of the trans-TaWox5 vectors of the varieties, such as Aikang 58, Jing 411 and Xinong 979, that cannot be transformed previously may reach over 10% respectively.

It can be seen that TaWox5 can greatly improve the transformation efficiency of wheat and solve the genotype problem of wheat transformation.

TABLE 1

Comparison of Transformation Efficiencies of Control Vector and TaWox5 Vector

| | pDE003 | | | pDE003- TaWox5 | | |
|---|---|---|---|---|---|---|
| Varieties | Number of immature embryos | Positive Plants | Transformation Efficiency (%) | Number of immature embryos | Positive Plants | Transformation Efficiency (%) |
| Kenong199 | 112 | 20 | 17.6 | 263 | 207 | 78.7 |
| Zhoumai18 | 335 | 48 | 14.3 | 333 | 573 | 172.1 |
| Lunxuan987 | 323 | 9 | 2.8 | 361 | 151 | 41.8 |
| Jingdong18 | 178 | 21 | 11.8 | 117 | 36 | 30.8 |

TABLE 1-continued

Comparison of Transformation Efficiencies of Control Vector and TaWox5 Vector

| | pDE003 | | | pDE003- TaWox5 | | |
|---|---|---|---|---|---|---|
| Varieties | Number of immature embryos | Positive Plants | Transformation Efficiency (%) | Number of immature embryos | Positive Plants | Transformation Efficiency (%) |
| Jimai22 | 342 | 19 | 5.5 | 2762 | 1333 | 48.3 |
| Zhongmai895 | 222 | 8 | 3.6 | 99 | 114 | 115.2 |
| AK58 | 434 | 0 | 0 | 88 | 10 | 11.4 |
| Yangmai16 | 196 | 5 | 2.6 | 85 | 22 | 25.9 |
| Jing411 | 305 | 4 | 1.3 | 141 | 29 | 20.6 |
| Xinchun9 | 165 | 22 | 13.3 | 73 | 52 | 71.2 |
| Fielder | 258 | 123 | 47.7 | 125 | 194 | 154.0 |
| Xinong 979 | 144 | 0 | 0 | 245 | 41 | 16.7 |
| Bs 366 | 272 | 0 | 0 | 84 | 50 | 59.5 |
| Sumai 3 | 150 | 4 | 2.67 | 284 | 166 | 58.5 |
| Sunstate | 113 | 0 | 0 | 224 | 26 | 11.6 |
| Ningchun 4 | 136 | 0 | 0 | 214 | 31 | 14.5 |
| Zhengmai 1860 | 84 | 4 | 4.8 | 300 | 73 | 24.3 |
| Chinese Spring | 124 | 0 | 0 | 96 | 12 | 12.5 |

Example 2

In this example, it was examined whether overexpression of TaWox5 and GUS gene as GOI leads to an increase in transformation efficiency using bombardment method in the wheat.

First, a callus was prepared from immature embryos of wheat (variety: Fielder) as follows. The wheat (variety: Fielder) callus was prepared according to Ke Wang, et al. (Ke Wang, Huiyun Liu, Lipu Du and Xingguo Ye (2017) Plant Biotechnology Journal 15, pp. 614-623) and Ishida, et al. (Ishida, Y., Tsunashima, M., Hiei, Y. and Komari, Y. (2015) Wheat (*Triticum aestivum* L.) transformation using immature embryos. In Agrobacterium Protocols: Volume 1. Methods in Molecular Biology, vol. 1223 (Wang, K., ed), pp. 189-198. New York: Springer Science+Business Media.), Immature embryos were isolated from the immature seeds under stereoscopic microscope. The embryos were transferred into WLS-Res medium without cefotaxime and carbenicillin. After 2 days the embryo axis was excised from the immature embryos using a scalpel and forceps and still put on WLS-Res medium without cefotaxime and carbenicillin for 5 days. The tissues were transferred onto callus-induction medium (WLS-P5) and cultivated for 2 weeks.

The plasmid containing TaWox5 and GUS gene as GOI was prepared as described hereafter. First, the plasmid containing GUS was prepared as pAH006 harboring GUS and bar (Yin Gui-xiang et al., (2014) Journal of Plant Genetic Resources, DOI:10.13430/j.cnki.jpgr.2014.06.022 三个方便实用的植物 表达载体构建与验证. The pDE003-TaWox5 prepared in Example 1 was also used in this experiment.

Transfer the pAH006 and pDE003-TaWox5, and pAH006 as negative control were transferred into the wheat (Fielder) callus by gene gun and then put on WLS-Res medium without cefotaxime and carbenicillin for another 5 days. The induction of genes using particle gun method was conducted according to Barcelo and Lazzeri (Plant Gene Transfer and Expression Protocols (1995) pp 113-123, Transformation of Cereals by Microprojectile Bombardment of Immature Inflorescence and Scutellum Tissues). The callus to which the vectors were induced was re-differentiated to obtain the transformed plant (trans-pAH006+pDE003-TaWox5 and trans-pAH006 as control), and then, the statistical analysis on transformation efficiency was conducted according to the Example 1.

As the result, the transformation efficiency of trans-pAH006+pDE003-TaWox5 was 9.55%, which was much higher than that of control, 4.04%. In addition, the transformants grew normally and their morphology without negative effect.

Example 3

In this example, it was examined whether overexpression of TaWox5 and GUS gene as GOI leads to an increase in transformation efficiency using mature embryos in the wheat.

First, a callus was prepared from mature embryos of wheat (variety: Fielder) as follows. Mature wheat (variety: Verry and CB037) grains were sterilized with 70% ethanol for 10 min, immersed into 25% bleach for 25 min and then soaked in sterile water overnight at 25° C. in the dark after being rinsed with sterile water three times. The slightly germinated seeds were sterilized again with 25% bleach for 15 min and then rinsed with sterile water three times.

The mature embryos in the seeds which were put onto sterile filter paper were scraped gently and fully into thin and small pieces (0.1 mm around in thickness and 0.5 mm around in diameter) with a sharp knife by back and forth for 5-6 times and the scraping tissues were inoculated softly on callus induction medium for one week.

The positive *Agrobacterium* strain was a recombinant bacterium obtained by transferring the recombinant plasmid pDE003-TaWox5 or empty pDE003 into *Agrobacterium* C58C1. The *Agrobacterium* C58C1 harboring pDE003-TaWox5 or empty pDE003 was infected to the callus, followed by the re-differentiation to obtain the transformed plants according to the Example 1. The statistical analysis on transformation efficiency in the transformed plants was conducted according to the Example 1.

The result was shown in Table 2. Although no transformant was obtained using the empty vector pDE003, some transformant was obtained and the transformation efficiency using the pDE003-TaWox5 was 1.19% and 1.81%, respectively. This result shows the TaWox5 gene can greatly improve the transformation efficiency of mature embryos in both varieties, Verry and CB037.

TABLE 2

| | PDE003 | | | pDE003-TaWox5 | | |
|---|---|---|---|---|---|---|
| Variety | Number of immature embryos | Positive Plants | Transformation Efficiency (%) | Number of immature embryos | Positive Plants | Transformation Efficiency (%) |
| Verry | 228 | 0 | 0 | 252 | 3 | 1.19 |
| CB037 | 381 | 0 | 0 | 441 | 8 | 1.81 |
| Total | 1218 | 0 | 0 | 1386 | 22 | 1.59 |

All of medium and the other steps were according to Medvecká and Harwood (2015) (Medvecká E. and Harwood W. A. (2015) Wheat (*Triticum aestivum* L.) transformation using mature embryos. In Agrobacterium Protocols: Volume 1. Methods in Molecular Biology, vol. 1223 (Wang, K., ed), pp. 199-209. New York: Springer Science+Business Media.)

In the comparative example without introduction of CB1 (gDNA), transformation did not occur at all. However, after the co-introduction of CB1, the transformation became possible.

Example 4

In this example, TaWox5, and a homologue of TaWox5 from a rice, OsWox5 were introduced into maize (varieties A188 and B73) by *Agrobacterium* method. The genes introduced were the following genes: gDNA of wheat TaWox5 obtained in the Example 1, cDNA synthesized according to information on the nucleotide sequence of TaWox5 (TaWox5cDNA) (SEQ ID NO: 11), gDNA of a homolog of TaWox5 from rice, OsWox5 (OsWox5gDNA) (SEQ ID NO: 3), and cDNA of OsWox5 (OsWox5cDNA) (SEQ ID NO: 12). In this example, TaWox5 obtained in the Example 1 was introduced by transformation with one vector having one T-DNA region, and the other genes were introduced using one vector, two T-DNA method that uses one vector having two T-DNA regions.

(1) Construction of the Vector

PCR reaction was carried out, by using pLC41 (LC215698.1) as a template, to replace the restriction enzymes AflII and PspOMI sites from 10667 to 52 of pLC41 (pLC41AflII-PspOMI).

Next, PCR reaction was carried out, by using pLC41AflII-PspOMI as a template to amplify RB-AflII-PspOMI-LB from about 330 bp upstream of RB to about 520 bp downstream of LB, and also by using pLC41 as a template to amplify pLC41KorB- to oriT from KorB to oriT. In the PCR reactions for RB-AflII-PspOMI-LB, a 5'-end phosphorylated primer consisting of a sequence encoding about 330 bp upstream portion of RB (pLC41 330 bp-RB F+P), and a 5'-end phosphorylated primer consisting of a sequence encoding about 520 bp downstream portion of the LB (pLC41 LB-520 bp R+P) were used. In the PCR reaction for pLC41 GUS-HPT KorB to oriT, a primer pLC41 oriT-IncC F consisting of a sequence encoding an interval oriT-IncC in downstream direction and a primer pLC41 oriT-IncC R consisting of a sequence encoding an interval oriT-IncC in upstream direction were used. As a result, a PCR product of 1100 bp from the RB-AflII-PspOMI-LB fragment, and a PCR product of about 10000 bp from pLC41KorB to oriT fragment were obtained.

RB-AflII-PspOMI-LB fragment and pLC41KorB to oriT fragment were ligated to yield pLC41 cotra AflII-PspOMI. The fragments containing OsWox5gDNA, OsWox5cDNA, TaWox5gDNA, or TaWox5cDNA were each synthesized using the primers described in Table 3, and inserted between ubiquitin promoter-ubiquitin intron and Nos terminator. In the first T-DNA of pLC41 cotra AflII-PspOMI, the maize ubiquitin promoter-ubiquitin intron—each TaWox5-Nos terminator expression cassette and 35s promoter-GUS-Nos terminator expression cassette were inserted from RB side. In the second T-DNA, the 35S promoter-Bar-35S terminator expression cassette was inserted.

TABLE 3

| Primer name | Sequence |
|---|---|
| TaWox5-FW | GGGGACAAGTTTGTACAAAAAAGCAGGCTA TGGAGGCGCTGAGCGGGCGG |
| TaWox5-RV | GGGGACCACTTTGTACAAGAAAGCTGGGTT TAGACCAGATACCGATCGAA |
| osTaWox5-FW | GGGGACAAGTTTGTACAAAAAAGCAGGCTA TGGAGGCTCTTAGCGGGCGAGTG |
| osTaWox5-RV | GGGGACCACTTTGTACAAGAAAGCTGGGTC TAGAGGCCGAAGCTGCAAAGCC |

(SEQ ID NOs: 13-16)

Thus prepared pLC41 OsWox5 cDNA-GUS-bar, pLC41-OsWox5 gDNA-GUS-bar, pLC41-TaWox5 cDNA-GUS-bar and pLC41-TaWox5gDNA-GUS-bar, and pDE003-TaWox5 prepared in the Example 1 as a vector having gDNA of TaWox5, and also a control vector (pLC41-GUS-bar) having Cauliflower mosaic virus 35s promoter-himacatalase intron-GUS-Nos terminator and maize ubiquitin promoter-ubiquitin intron-bar-Nos terminator on T-DNA were subjected to testing. Each of these vectors was introduced into *Agrobacterium tumefaciens* LBA4404 strain with pVGW9.

(2) Transformation of Maize 1

The LBA4404 strain introduced by pDE003-TaWox5, pLC41-TaWox5cDNA-GUS-bar, pLC41-TaWox5gDNA-GUS-bar, or pLC41-GUS-bar, and pVGW9 were inoculated into immature embryos of maize (variety: B73). The inoculation and co-cultivation were conducted according to the method of Ishida et al., (2007) NATURE PROTOCOLS, Vol. 2, No. 7, 1614-1621.

At day 5 of co-cultivation (day 7 post-inoculation), the number of immature embryos which formed a compact callus on scutellum surface was counted. The result was shown in Table 4. In the immature embryos inoculated with a control pLC41-GUS-bar, immature embryos forming a compact callus was not seen at all. In contrast, in the immature embryos transformed with the vector containing TaWox5 gene, immature embryos forming a compact callus were observed at efficiency from 12 to 86.2%. These callus proliferated by continued cultivation. And the regenerated plants were obtained from the proliferated callus, by transferring and cultivating such callus on regeneration culture. It was confirmed that these regenerated plants could root and could grow in the green house by transferring to the soil in pot.

TABLE 4

| Introduced vector | Number of immature embryos | Number of callus formation | Callus formation efficiency (%) |
|---|---|---|---|
| pLC41-GUS-bar | 23 | 0 | 0 |
| pDE003-TaWox5 | 25 | 3 | 12.0 |
| pLC41-TaWox5cDNA-GUS-bar | 29 | 25 | 86.2 |
| pLC41-TaWox5gDNA-GUS-bar | 29 | 15 | 51.7 |

(3) Transformation of Maize 2

The LBA4404 strain introduced by pLC41 OsWox5cDNA-GUS-bar, pLC41 OsWox5gDNA-GUS-bar, pLC41-TaWox5cDNA-GUS-bar, or pLC41-GUS-bar, and pVGW9 were inoculated into immature embryos of maize (variety: B73). The inoculation and co-cultivation were conducted according to the method of Ishida et al., NATURE PROTOCOLS, 2007, Vol. 2, No. 7, 1614-1621.

At day 5 of co-cultivation (day 7 post-inoculation), the number of immature embryo forming a compact callus on scutellum surface was counted. The result was shown in Table 5. In the immature embryos inoculated with a control pLC41-GUS-bar, immature embryos forming a compact callus was not seen at all. In contrast, in the immature embryos transformed with vectors comprising various TaWox5 genes, immature embryos forming a compact callus were observed at efficiency from 32.1 to 85.2%.

TABLE 5

| Introduced vector | Number of immature embryos | Number of callus formation | Callus formation efficiency (%) |
|---|---|---|---|
| pLC41-GUS-bar | 28 | 0 | 0 |
| pLC41-osTaWox5cDNA-GUS-bar | 27 | 21 | 77.8 |
| pLC41-osTaWox5gDNA-GUS-bar | 28 | 9 | 32.1 |
| pLC41-TaWox5gDNA-GUS-bar | 27 | 23 | 85.2 |

(4) Transformation of Maize 3

The LBA4404 strain introduced by pLC41 OsWox5c-DNA-GUS-bar or pLC41-TaWox5cDNA-GUS-bar, and pVGW9 were inoculated into immature embryos of maize (variety: A188). The inoculation and co-cultivation, selection and re-differentiation were conducted according to the method of Ishida et al., NATURE PROTOCOLS, 2007, Vol. 2, No. 7, 1614-1621.

The part of re-differentiated plant leaves were cut and the expression of the GUS gene was examined. The examination of the GUS gene expression was conducted according to the method of Ishida et al., NATURE PROTOCOLS, 2007, Vol. 2, No. 7, 1614-1621. In the leaves of the re-differentiated plants obtained from immature embryos which were inoculated with either of the vectors, both of the leaves were found to be blue staining. Thus, it was confirmed that re-differentiated plants can be obtained from immature embryos transformed with various TaWox5, without excluding TaWox5 gene.

As mentioned above, in the method of the present invention, the callus formation and regeneration in maize B73 variety, which is known as "difficult-to-culture" variety, was observed. Further, in the maize variety A188, the callus efficiency was improved, and even the re-differentiation was successful without removing the TaWox5 gene. Similar effects were observed when either WOX5 related gene from wheat and WOX5 related gene from rice were used. Further, it was observed that either use of gDNA and cDNA are also effective.

Example 5

In this example, the chimeric proteins of TaWox5 protein and GFP protein: 3'-TaWox5-GFP-5' and 3'-GFP-TaWox5-5', were expressed in wheat. In both cases, the TaWox5 and GFP were combined via a linker consisting of 10 Gly residues. All sequence data for the primers used in this Example is shown in Table 6.

TABLE 6

| Primer name | Sequence |
|---|---|
| GFPbamFinf4 | CAGGTCGACTCTAGAGGAATGGTGAGCAAG GGCGAG |
| GFPbamRinf4 | TTCGAGCTCGGTACCCGGGGAtccaccacc gccacctccgccaccgcctccAGATCTGTA CAGCTCG |
| Wox5bamFinf3 | CAGGTCGACTCTAGAGGAATGGAGGCGCTG AGCGG |
| Wox5bamRinf3 | TTCGAGCTCGGTACCCGGGGAtccaccacc gccacctccgccaccgcctccGACCAGATA CCGAT |
| Wox5Finf4 | gcggaggtggcggtggtggaATGGAGGCGC TGAGCGG |
| Wox5Rinf4 | TTCGAGCTCGGTACCCGGGGATTAGACCAG ATACCGAT |
| GFPFinf3 | gcggaggtggcggtggtggaATGGTGAGCA AGGGCGAG |
| GFPRinf3 | TTCGAGCTCGGTACCCGGGGATTAAGATCT GTACAGCTCG |

(SEQ ID NOs: 17-24)

Figure 5:
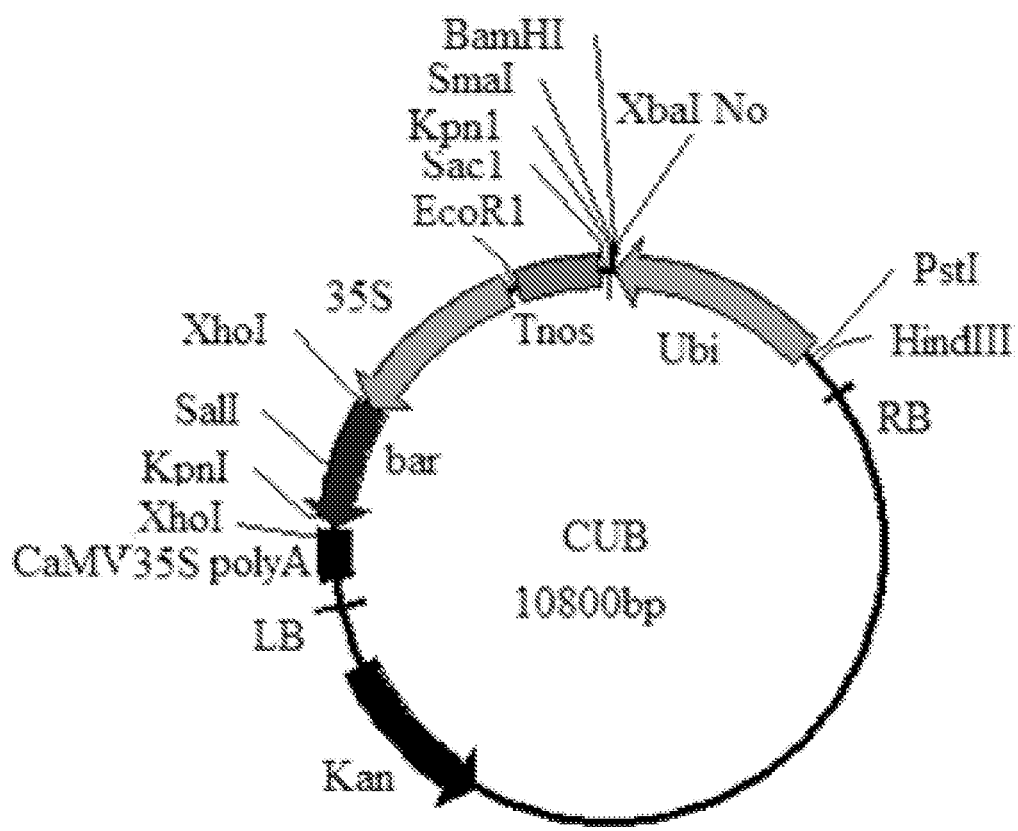
FIG. 5 is a schematic diagram of a pCUB vector.

To construct a vector harboring chimeric protein, first, the fragment harboring GFP gene with BamH1 site and 10 Gly linker and the fragment harboring TaWox5 gene with BamH1 site and 10 Gly linker were obtained using the primers GFPbamFinf4 and GFPbamRinf4, Wox5bamFinf3 and Wox5bamRinf3, respectively. Then the GFP fragment, TaWox5 fragment and pCUB vector (shown in FIG. 5) were digested with BamHI, followed by the ligation between the fragment containing GUS and digested pCUB to obtain the pCUB-10 Gly-GFP and pCUB-10 Gly-TaWox5.

(1) For the construction of a vector for expressing 5'-TaWox5-(10 Gly)-GFP-3'; The fragment harboring TaWox5 gene without stop codon was amplified using Wox5Finf4 and Wox5Rinf4 as primers. Such fragment and digested pCUB-10Gly-GFP by BamHI were ligated to obtain pCUB-TaWox5-10Gly-GFP by homologous recombination.

(2) For the construction of a vector for expressing 5'-GFP-(10 Gly)-TaWox5-3'; The fragment harboring GFP gene without stop codon was amplified using GFPFinf3 and GFPRinf3 as primers. Such fragment and digested pCUB-10Gly-TaWox5 by BamHI were ligated to obtain pCUB-GFP-10Gly-TaWox5 by homologous recombination.

These vectors pCUB-GFP-10Gly-TaWox5, pCUB-TaWox5-10Gly-GFP and empty pCUB were introduced into the immature embryos of wheat (variety: Jimai22) followed by the re-differentiation to obtain transformants and the statistical analysis on transformation efficiency. The procedure for transforming plants and the statistical analysis were conducted according to the Example 1. As the result, the transformation efficiency of pCUB-TaWox5-10Gly-GFP was 39.6% although that of pCUB-GFP-10Gly-TaWox5 and empty pCUB were 0%, no transformants was obtained.

SEQUENCE LISTING

The invention claimed is:

1. A method for improving transformation efficiency of a plant, comprising:
   (a) introducing into a plant
      (1) a nucleic acid construct that comprises a nucleic acid encoding a polypeptide comprising the amino acid sequence according to SEQ ID NO: 2, and a promoter for producing said first nucleic acid in a plant, wherein said promoter is heterologous with respect to said nucleic acid; and
      (2) a desired nucleic acid to be expressed in the plant; and
   (b) selecting from a plurality of cells of said plant a transformed plant cell with an improved transformation efficiency, wherein the improvement comprises at least one improvement selected from the group consisting of:
      a) improvement of efficiency of callus formation of the plant;
      b) improvement of redifferentiation rate of the plant; and
      c) improvement of gene transfer efficiency.

2. The method for transformation according to claim 1, wherein the desired nucleic acid to be produced in the plant is transiently expressed.

* * * * *

```
                              SEQUENCE LISTING

<160> NUMBER OF SEQ ID NOS: 24

<210> SEQ ID NO 1
<211> LENGTH: 13202
<212> TYPE: DNA
<213> ORGANISM: Triticum aestivum
<220> FEATURE:
<221> NAME/KEY: misc_feature
<222> LOCATION: (6734)..(6982)
<223> OTHER INFORMATION: n is a, c, g, or t
<220> FEATURE:
<221> NAME/KEY: misc_feature
<222> LOCATION: (8720)..(8720)
<223> OTHER INFORMATION: n is a, c, g, or t
<220> FEATURE:
<221> NAME/KEY: misc_feature
<222> LOCATION: (8802)..(8802)
<223> OTHER INFORMATION: n is a, c, g, or t
<220> FEATURE:
<221> NAME/KEY: misc_feature
<222> LOCATION: (10827)..(10827)
<223> OTHER INFORMATION: n is a, c, g, or t
<220> FEATURE:
<221> NAME/KEY: misc_feature
<222> LOCATION: (10909)..(10909)
<223> OTHER INFORMATION: n is a, c, g, or t

<400> SEQUENCE: 1
agtactttga tccaacccct ccgctgctat agtgcagtcg gcttctgacg ttcagtgcag      60
ccgtcttctg aaaacgacat gtcgcacaag tcctaagtta cgcgacaggc tgccgccctg     120
cccttttcct ggcgttttct tgtcgcgtgt tttagtcgca taaagtagaa tacttgcgac     180
tagaaccgga gacattacgc catgaacaag agcgccgccg ctggcctgct gggctatgcc     240
cgcgtcagca ccgacgacca ggacttgacc aaccaacggg ccgaactgca cgcggccggc     300
tgcaccaagc tgttttccga aagatcacc ggcaccaggc gcgaccgccc ggagctggcc     360
aggatgcttg accacctacg ccctggcgac gttgtgacag tgaccaggct agaccgcctg     420
gcccgcagca cccgcgacct actggacatt gccgagcgca tccaggaggc cggcgcgggc     480
ctgcgtagcc tggcagagcc gtgggccgac accaccacgc cggccggccg catggtgttg     540
accgtgttcg ccggcattgc cgagttcgag cgttccctaa tcatcgaccg cacccggagc     600
gggcgcgagg ccgccaaggc ccgaggcgtg aagtttggcc ccgccctac cctcaccccg     660 gcacagatcg cgcacgcccg cgagctgatc gaccaggaag ccgcaccgt gaaagaggcg     720 gctgcactgc ttggcgtgca tcgctcgacc ctgtaccgcg cacttgagcg cagcgaggaa     780
gtgacgccca ccgaggccag gcggcgcggt gccttccgtg aggacgcatt gaccgaggcc     840
gacgccctgg cggccgccga gaatgaacgc caagaggaac aagcatgaaa ccgcaccagg     900
acggccagga cgaaccgttt ttcattaccg aagagatcga gcggagatg atcgcggccg     960 ggtacgtgtt cgagccgccc gcgcacgtct caaccgtgcg gctgcatgaa atcctggccg    1020
gtttgtctga tgccaagctg gcggcctggc cggccagctt ggccgctgaa gaaaccgagc    1080
gccgccgtct aaaaaggtga tgtgtatttg agtaaaacag cttgcgtcat gcggtcgctg    1140
cgtatatgat gcgatgagta aataaacaaa tacgcaaggg gaacgcatga aggttatcgc    1200
tgtacttaac cagaaaggcg ggtcaggcaa gacgaccatc gcaacccatc tagcccgcgc    1260
cctgcaactc gccggggccg atgttctgtt agtcgattcc gatccccagg gcagtgcccg    1320
cgattgggcg gccgtgcggg aagatcaacc gctaaccgtt gtcggcatcg accgcccgac    1380
gattgaccgc gacgtgaagg ccatcggccg gcgcgacttc gtagtgatcg acggagcgcc    1440
```

```
ccaggcggcg gacttggctg tgtccgcgat caaggcagcc gacttcgtgc tgattccggt    1500
gcagccaagc ccttacgaca tatgggccac cgccgacctg gtggagctgg ttaagcagcg    1560
cattgaggtc acggatggaa ggctacaagc ggcctttgtc gtgtcgcggg cgatcaaagg    1620
cacgcgcatc ggcggtgagg ttgccgaggc gctggccggg tacgagctgc ccattcttga    1680
gtcccgtatc acgcagcgcg tgagctaccc aggcactgcc gccgccggca aaccgttct    1740
tgaatcagaa cccgagggcg acgctgcccg cgaggtccag gcgctggccg ctgaaattaa    1800
atcaaaactc atttgagtta atgaggtaaa gagaaaatga gcaaaagcac aaacacgcta    1860
agtgccggcc gtccgagcgc acgcagcagc aaggctgcaa cgttggccag cctggcagac    1920
acgccagcca tgaagcgggt caactttcag ttgccggcgg aggatcacac caagctgaag    1980
atgtacgcgg tacgccaagg caagaccatt accgagctgc tatctgaata catcgcgcag    2040
ctaccagagt aaatgagcaa atgaataaat gagtagatga attttagcgg ctaaaggagg    2100
cggcatggaa aatcaagaac aaccaggcac cgacgccgtg gaatgcccca tgtgtggagg    2160
aacgggcggt tggccaggcg taagcggctg ggttgtctgc cggccctgca atggcactgg    2220
aaccccaag cccgaggaat cggcgtgacg gtcgcaaacc atccggcccg gtacaaatcg    2280
gcgcggcgct gggtgatgac ctggtggaga agttgaaggc cgcgcaggcc gcccagcggc    2340
aacgcatcga ggcagaagca cgccccggtg aatcgtggca agcggccgct gatcgaatcc    2400
gcaaagaatc ccggcaaccg ccggcagccg gtgcgccgtc gattaggaag ccgcccaagg    2460
gcgacgagca accagatttt ttcgttccga tgctctatga cgtgggcacc cgcgatagtc    2520
gcagcatcat ggacgtggcc gttttccgtc tgtcgaagcg tgaccgacga gctggcgagg    2580
tgatccgcta cgagcttcca gacgggcacg tagaggtttc gcagggccg gccggcatgg    2640
ccagtgtgtg ggattacgac ctggtactga tggcggtttc ccatctaacc gaatccatga    2700
accgataccg ggaagggaag ggagacaagc ccggccgcgt gttccgtcca cacgttgcgg    2760
acgtactcaa gttctgccgg cgagccgatg gcggaaagca gaaagacgac ctggtagaaa    2820
cctgcattcg gttaaacacc acgcacgttg ccatgcagcg tacgaagaag gccaagaacg    2880
gccgcctggt gacggtatcc gagggtgaag ccttgattag ccgctacaag atcgtaaaga    2940
gcgaaaccgg gcggccggag tacatcgaga tcgagctagc tgattggatg taccgcgaga    3000
tcacagaagg caagaacccg gacgtgctga cggttcaccc cgattacttt ttgatcgatc    3060
ccggcatcgg ccgttttctc taccgcctgg cacgccgcgc cgcaggcaag gcagaagcca    3120
gatggttgtt caagacgatc tacgaacgca gtggcagcgc cggagagttc aagaagttct    3180
gtttcaccgt gcgcaagctg atcgggtcaa atgacctgcc ggagtacgat ttgaaggagg    3240
aggcggggca ggctggcccg atcctagtca tgcgctaccg caacctgatc gagggcgaag    3300
catccgccgg ttcctaatgt acggagcaga tgctagggca aattgcccta gcagggaaa    3360
aaggtcgaaa aggtctcttt cctgtggata gcacgtacat tgggaaccca aagccgtaca    3420
ttgggaaccg gaacccgtac attgggaacc caaagccgta cattgggaac cggtcacaca    3480
tgtaagtgac tgatataaaa gagaaaaaag gcgattttc cgcctaaaac tctttaaaac    3540
ttattaaaac tcttaaaacc cgcctggcct gtgcataact gtctggccag cgcacagccg    3600
aagagctgca aaaagcgcct acccttcggt cgctgcgctc cctacgcccc gccgcttcgc    3660
gtcggcctat cgcggccgct ggccgctcaa aaatggctgg cctacggcca ggcaatctac    3720
cagggcgcgg acaagccgcg ccgtcgccac tcgaccgccg cgcccacat caaggcaccc    3780
```

```
tgcctcgcgc gtttcggtga tgacggtgaa aacctctgac acatgcagct cccggagacg    3840
gtcacagctt gtctgtaagc ggatgccggg agcagacaag cccgtcaggg cgcgtcagcg    3900
ggtgttggcg ggtgtcgggg cgcagccatg acccagtcac gtagcgatag cggagtgtat    3960
actggcttaa ctatgcggca tcagagcaga ttgtactgag agtgcaccat atgcggtgtg    4020
aaataccgca cagatgcgta aggagaaaat accgcatcag gcgctcttcc gcttcctcgc    4080
tcactgactc gctgcgctcg gtcgttcggc tgcggcgagc ggtatcagct cactcaaagg    4140
cggtaatacg gttatccaca gaatcagggg ataacgcagg aaagaacatg tgagcaaaag    4200
gccagcaaaa ggccaggaac cgtaaaaagg ccgcgttgct ggcgtttttc cataggctcc    4260
gcccccctga cgagcatcac aaaaatcgac gctcaagtca gaggtggcga aacccgacag    4320
gactataaag ataccaggcg tttccccctg gaagctccct cgtgcgctct cctgttccga    4380
ccctgccgct taccggatac ctgtccgcct ttctcccttc gggaagcgtg gcgctttctc    4440
atagctcacg ctgtaggtat ctcagttcgg tgtaggtcgt tcgctccaag ctgggctgtg    4500
tgcacgaacc ccccgttcag cccgaccgct gcgccttatc cggtaactat cgtcttgagt    4560
ccaacccggt aagacacgac ttatcgccac tggcagcagc cactggtaac aggattagca    4620
gagcgaggta tgtaggcggt gctacagagt tcttgaagtg gtggcctaac tacggctaca    4680
ctagaaggac agtatttggt atctgcgctc tgctgaagcc agttaccttc ggaaaaagag    4740
ttggtagctc ttgatccggc aaacaaacca ccgctggtag cggtggtttt tttgtttgca    4800
agcagcagat tacgcgcaga aaaaaggat ctcaagaaga tcctttgatc ttttctacgg    4860
ggtctgacgc tcagtggaac gaaaactcac gttaagggat tttggtcatg catgatatat    4920
ctcccaattt gtgtagggct tattatgcac gcttaaaaat aataaaagca gacttgacct    4980
gatagtttgg ctgtgagcaa ttatgtgctt agtgcatcta atcgcttgag ttaacgccgg    5040
cgaagcggcg tcggcttgaa cgaatttcta gctagacatt atttgccgac taccttggtg    5100
atctcgcctt tcacgtagtg acaaattct tccaactgat ctgcgcgcga ggccaagcga    5160
tcttcttctt gtccaagata agcctgtcta gcttcaagta tgacgggctg atactgggcc    5220
ggcaggcgct ccattgccca gtcggcagcg acatccttcg gcgcgatttt gccggttact    5280
gcgctgtacc aaatgcggga caacgtaagc actacatttc gctcatcgcc agcccagtcg    5340
ggcggcgagt tccatagcgt taaggtttca tttagcgcct caaatagatc ctgttcagga    5400
accggatcaa agagttcctc cgccgctgga cctaccaagg caacgctatg ttctcttgct    5460
tttgtcagca agatagccag atcaatgtcg atcgtggctg gctcgaagat acctgcaaga    5520
atgtcattgc gctgccattc tccaaattgc agttcgcgct tagctggata acgccacgga    5580
atgatgtcgt cgtgcacaac aatggtgact tctacagcgc ggagaatctc gctctctcca    5640
ggggaagccg aagtttccaa aggtcgttg atcaaagctc gccgcgttgt tcatcaagc    5700 cttacggtca ccgtaaccag caaatcaata tcactgtgtg gcttcaggcc gccatccact    5760
gcggagccgt acaaatgtac ggccagcaac gtcggttcga gatggcgctc gatgacgcca    5820
actacctctg atagttgagt cgatacttcg gcgatcaccg cttcccccat gatgtttaac    5880
tttgttttag ggcgactgcc ctgctgcgta acatcgttgc tgctccataa catcaaacat    5940
cgacccacgg cgtaacgcgc ttgctgcttg gatgcccgag gcatagactg taccccaaaa    6000
aaacatgtca taacaagaag ccatgaaaac cgccactgcg ccgttaccac cgctgcgttc    6060
ggtcaaggtt ctggaccagt tgcgtgacgg cagttacgct acttgcatta cagcttacga    6120
accgaacgag gcttatgtcc actgggttcg tgccgaatt gatcacaggc agcaacgctc    6180
```

-continued

```
tgtcatcgtt acaatcaaca tgctaccctc cgcgagatca tccgtgtttc aaacccggca    6240
gcttagttgc cgttcttccg aatagcatcg gtaacatgag caaagtctgc cgccttacaa    6300
cggctctccc gctgacgccg tcccggactg atgggctgcc tgtatcgagt ggtgattttg    6360
tgccgagctg ccggtcgggg agctgttggc tggctggtgg caggatatat tgtggtgtaa    6420
acaaattgac gcttagacaa cttaataaca cattgcggac gttttttaatg tactgaatta    6480 acgccgaatt gctctagcca atacgcaaac cgcctctccc cgcgcgttgg ccgattcatt    6540
aatgcagctg gcacgacagg tttcccgact ggaaagcggg cagtgagcgc aacgcaatta    6600
atgtgagtta gctcactcat taggcacccc aggctttaca ctttatgctt ccggctcgta    6660
tgttgtgtgg aattgtgagc ggataacaat ttcacacagg aaacagctat gaccatgatt    6720
acgaattcga gctnnnnnnn nnnnnnnnnn nnnnnnnnnn nnnnnnnnnn nnnnnnnnnn    6780
nnnnnnnnnn nnnnnnnnnn nnnnnnnnnn nnnnnnnnnn nnnnnnnnnn nnnnnnnnnn    6840
nnnnnnnnnn nnnnnnnnnn nnnnnnnnnn nnnnnnnnnn nnnnnnnnnn nnnnnnnnnn    6900
nnnnnnnnnn nnnnnnnnnn nnnnnnnnnn nnnnnnnnnn nnnnnnnnnn nnnnnnnnnn    6960
nnnnnnnnnn nnnnnnnnnn nngagctccg atctagtaac atagatgaca ccgcgcgcga    7020
taatttatcc tagtttgcgc gctatatttt gttttctatc gcgtattaaa tgtataattg    7080
cgggactcta atcataaaaa cccatctcat aaataacgtc atgcattaca tgttaattat    7140
tacatgctta acgtaattca acagaaatta tatgataatc atcgcaagac cggcaacagg    7200
attcaatctt aagaaacttt attgccaaat gtttgaacga tctgcaggtc gacggatcag    7260
atctcggtga cgggcaggac cggacggggc ggtaccggca ggctgaagtc cagctgccag    7320
aaacccacgt catgccagtt cccgtgcttg aagccggccg cccgcagcat gccgcggggg    7380
gcatatccga gcgcctcgtg catgcgcacg ctcgggtcgt tgggcagccc gatgacagcg    7440
accacgctct tgaagccctg tgcctccagg gacttcagca ggtgggtgta gagcgtggag    7500
cccagtcccg tccgctggtg gcgggggggag acgtacacgg tcgactcggc cgtccagtcg    7560
taggcgttgc gtgccttcca ggggcccgcg taggcgatgc cggcgacctc gccgtccacc    7620
tcggcgacga gccagggata cgctcccgc agacggacga ggtcgtccgt ccactcctgc    7680
ggttcctgcg gctcggtacg gaagttgacc gtgcttgtct cgatgtagtg gttgacgatg    7740
gtgcagaccc ccggcatgtc cgcctcggtg gcacggcgga tgtcggccgg gcgtcgttct    7800
gggctcatgg atcctctaga gtcgacctgc agaagtaaca ccaaacaaca gggtgagcat    7860
cgacaaaaga aacagtacca agcaaataaa tagcgtatga aggcagggct aaaaaaatcc    7920
acatatagct gctgcatatg ccatcatcca agtatatcaa gatcaaaata attataaaac    7980
atacttgttt attataatag ataggtactc aaggttagag catatgaata gatgctgcat    8040
atgccatcat gtatatgcat cagtaaaacc cacatcaaca tgtataccta tcctagatcg    8100
atatttccat ccatcttaaa ctcgtaacta tgaagatgta tgacacacac atacagttcc    8160
aaaattaata aatacaccag gtagtttgaa acagtattct actccgatct agaacgaatg    8220
aacgaccgcc caaccacacc acatcatcac aaccaagcga acaaaaagca tctctgtata    8280
tgcatcagta aaacccgcat caacatgtat acctatccta gatcgatatt tccatccatc    8340
atcttcaatt cgtaactatg aatatgtatg gcacacacat acagatccaa aattaataaa    8400
tccaccaggt agtttgaaac agaattaatt ctactccgat ctagaacgac cgcccaacca    8460
gaccacatca tcacaaccaa gacaaaaaaa agcatgaaaa gatgacccga caaacaagtg    8520
```

```
cacggcatat attgaaataa aggaaaaggg caaaccaaac cctatgcaac gaaacaaaaa    8580
aaatcatgaa atcgatcccg tctgcggaac ggctagagcc atcccaggat tccccaaaga    8640
gaaacactgg caagttagca atcagaacgt gtctgacgta caggtcgcat ccgtgtacga    8700
acgctagcag cacggatctn acacaaacac ggatctaaca caaacatgaa cagaagtaga    8760
ctaccgggcc ctaacatgga ccgaacgcga tctagagagt anagagggggg ggggggggagg  8820 acgagcggcg taccttgaag cggaggtgcc gacgggtgga tttggggggag atctggtttg   8880 tgtgtgtgtg cgctccgaac aacacgaggt tggggaaaga gggtgtggag ggggtgtcta    8940
tttattacgg cgggcgagga agggaaagcg aaggagcggt gggaaaggaa tcccccgtag    9000
ctgccggtgc cgtgagagga ggaggaggcc gcctgccgtg ccggctcacg tctgccgctc    9060
cgccacgcaa tttctggatg ccgacagcgg agcaagtcca acggtggagc ggaactctcg    9120 agagggtcc agaggcagcg acagagatgc cgtgccgtct gcttcgcttg gcccgacgcg     9180
acgctgctgg ttcgctggtt ggtgtccgtt agactcgtcg acgcgtttta acaggctggc    9240
attatctact cgaaacaaga aaaatgtttc cttagttttt ttaatttctt aaagggtatt    9300
tgtttaattt ttagtcactt tattttattc tattttatat ctaaattatt aaataaaaaa    9360
actaaaatag agttttagtt ttcttaattt agaggctaaa atagaataaa atagatgtac    9420
taaaaaaatt agtctataaa aaccattaac cctaaacct aaatggatgt actaataaaa     9480
tggatgaagt attatatagg tgaagctatt tgcaaaaaaa aaggagaaca catgcacact    9540
aaaaagataa aactgtagag tcctgttgtc aaaatactca attgtccttt agaccatgtc    9600
taactgttca tttatatgat tctctaaaac actgatatta ttgtagtact atagattata    9660
ttattcgtag agtaaagttt aaatatatgt ataagatag ataaactgca cttcaaacaa     9720
gtgtgacaaa aaaaatatgt ggtaattttt tataacttag acatgcaatg ctcattatct    9780
ctagagaggg gcacgaccgg gtcacgctgc aaagctttgc agcgtgaccc ggtcgtgccc    9840
ctctctagag ataatgagca ttgcatgtct aagttataaa aaattaccac atatttttt     9900 tgtcacactt gtttgaagtg cagtttatct atctttatac atatatttaa actttactct    9960
acgaataata taatctatag tactacaata atatcagtgt tttagagaat catataaatg    10020
aacagttaga catggtctaa aggacaattg agtattttga caacaggact ctacagtttt    10080 atcttttag tgtgcatgtg ttctcctttt tttttgcaaa tagcttcacc tatataatac     10140
ttcatccatt ttattagtac atccatttag ggtttagggt taatggtttt tatagactaa    10200
tttttttagt acatctattt tattctattt tagcctctaa attaagaaaa ctaaaactct    10260
attttagttt ttttattaa taatttagat ataaaataga ataaaataaa gtgactaaaa     10320
attaaacaaa tacccttaa gaaattaaaa aaactaagga acattttttc ttgtttcgag     10380
tagataatgc cagcctgtta aacgccgtcg acgagtctaa cggacaccaa ccagcgaacc    10440
agcagcgtcg cgtcgggcca agcgaagcag acggcacggc atctctgtcg ctgcctctgg    10500 accccctctcg agagttccgc tccaccgttg gacttgctcc gctgtcggca tccagaaatt    10560
gcgtggcgga gcggcagacg tgagccggca cggcaggcgg cctcctcctc ctctcacggc    10620
accggcagct acgggggatt cctttcccac cgctccttcg ctttcccttc ctcgcccgcc    10680
gtaataaata gacacccct ccacaccctc tttccccaac ctcgtgttgt tcggagcgca     10740
cacacacaca aaccagatct cccccaaatc caccgtcgg cacctccgct tcaaggtacg     10800
ccgctcgtcc tccccccccc ccctctntac tctctagatc gcgttcggtc catgttaggg    10860
cccggtagtc tacttctgtt catgtttgtg ttagatccgt gtttgtgtna gatccgtgct    10920
```

```
gctagcgttc gtacacggat gcgacctgta cgtcagacac gttctgattg ctaacttgcc  10980
agtgtttctc tttggggaat cctgggatgg ctctagccgt tccgcagacg ggatcgattt  11040
catgatttt  tttgtttcgt tgcatagggt ttggtttgcc cttttccttt atttcaatat  11100
atgccgtgca cttgtttgtc gggtcatctt ttcatgcttt tttttgtctt ggttgtgatg  11160
atgtggtctg gttgggcggt cgttctagat cggagtagaa ttaattctgt ttcaaactac  11220
ctggtggatt tattaatttt ggatctgtat gtgtgtgcca tacatattca tagttacgaa  11280
ttgaagatga tggatggaaa tatcgatcta ggataggtat acatgttgat gcgggtttta  11340
ctgatgcata tacagagatg cttttttgttc gcttggttgt gatgatgtgg tgtggttggg  11400
cggtcgttca ttcgttctag atcggagtag aatactgttt caaactacct ggtgtattta  11460
ttaattttgg aactgtatgt gtgtgtcata catcttcata gttacgagtt taagatggat  11520
ggaaatatcg atctaggata ggtatacatg ttgatgtggg ttttactgat gcatatacat  11580
gatggcatat gcagcatcta ttcatatgct ctaaccttga gtacctatct attataataa  11640
acaagtatgt tttataatta ttttgatctt gatatacttg gatgatggca tatgcagcag  11700
ctatatgtgg attttttag ccctgccttc atacgctatt tatttgcttg gtactgtttc  11760
ttttgtcgat gctcaccctg ttgtttggtg ttacttctgc aggtcgactc tagaggatcc  11820
cgggatggag gcgctgagcg ggcgggtggg agtgaagtgc gggcggtgga acccgacggc  11880
ggagcaggtg aaggtgctga cggagctgtt ccggcgggg  ctgcggacgc cgagcaccga  11940
gcagatccag cggatctcca cccacctcag cgccttcggc aaggtggaga gcaagaacgt  12000
cttctactgg ttccagaacc acaaggcccg cgagcgccac caccacaaga agcgccgccg  12060
cgtcgcatcc tgctcccccg acagcagcag caacgatgaa gagaccggcc gtgccgccgc  12120
cgccgagccc gccgacctcg tgctccagcc tcccgagagc aagcgggagg ccggaggcta  12180
caaccaccac ccccgatca tgacatgtaa gttagcagta gcacccatgt cgttgttcat  12240
acgtagagct tggttttgttc ctaatggaac agtatcctta gatcatcggc ccggtgctga  12300
tccatttggt gcgtgcatgc aggctatgtg agggaggtgg cggagcagga agaggcgacg  12360
acgtgggagc ggccgacgag ggaagtggag acgctggagc tgttcccgct caaagcagcc  12420
tgctacgacc tggagctgga ggcggacagg ttcagccggt atgtgaggag cggcgagcaa  12480
cagtgcaggg agatctcctt cttcgacgtg gccaccggac gggatccgcc gctggagctc  12540
aggctctgca gcttcgatcg gtatctggtc taaggtaccg agctgatcgt tcaaacattt  12600
ggcaataaag tttcttaaga ttgaatcctg ttgccggtct tgcgatgatt atcatataat  12660
ttctgttgaa ttacgttaag catgtaataa ttaacatgta atgcatgacg ttatttatga  12720
gatgggtttt tatgattaga gtcccgcaat tatacattta atacgcgata gaaaacaaaa  12780
tatagcgcgc aaactaggat aaattatcgc gcgcggtgtc atctatgtta ctagatcgaa  12840
ttcaagcttg gcactggccg tcgttttaca acgtcgtgac tgggaaaacc ctggcgttac  12900
ccaacttaat cgccttgcag cacatccccc tttcgccagc tggcgtaata gcgaagaggc  12960
ccgcaccgat cgcccttccc aacagttgcg cagcctgaat ggcgaatgag cttgagcttg  13020
gatcagattg tcgtttcccg ccttcagttt aaactatcag tgtttgacag gatatattgg  13080
cgggtaaacc taagagaaaa gagcgtttat tagaataacg gatatttaaa agggcgtgaa  13140
aaggtttatc cgttcgtcca tttgtatgtg catgccaacc acagggttcc cctcgggatc  13200
aa                                                                 13202
```

<210> SEQ ID NO 2
<211> LENGTH: 210
<212> TYPE: PRT
<213> ORGANISM: Triticum aestivum

<400> SEQUENCE: 2

```
Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Thr His Leu
        35                  40                  45

Ser Ala Phe Gly Lys Val Glu Ser Lys Asn Val Phe Tyr Trp Phe Gln
    50                  55                  60

Asn His Lys Ala Arg Glu Arg His His Lys Lys Arg Arg Arg Arg Val
65                  70                  75                  80

Ala Ser Cys Ser Pro Asp Ser Ser Asn Asp Glu Glu Thr Gly Arg
                85                  90                  95

Ala Ala Ala Ala Glu Pro Ala Asp Leu Val Leu Gln Pro Pro Glu Ser
            100                 105                 110

Lys Arg Glu Ala Gly Gly Tyr Asn His His Pro Arg Ile Met Thr Cys
        115                 120                 125

Tyr Val Arg Glu Val Ala Glu Gln Glu Ala Thr Thr Trp Glu Arg
    130                 135                 140

Pro Thr Arg Glu Val Glu Thr Leu Glu Leu Phe Pro Leu Lys Ala Ala
145                 150                 155                 160

Cys Tyr Asp Leu Glu Leu Glu Ala Asp Arg Phe Ser Arg Tyr Val Arg
                165                 170                 175

Ser Gly Glu Gln Gln Cys Arg Glu Ile Ser Phe Phe Asp Val Ala Thr
            180                 185                 190

Gly Arg Asp Pro Pro Leu Glu Leu Arg Leu Cys Ser Phe Asp Arg Tyr
        195                 200                 205

Leu Val
    210
```

<210> SEQ ID NO 3
<211> LENGTH: 712
<212> TYPE: DNA
<213> ORGANISM: rice

<400> SEQUENCE: 3

```
atggaggctc ttagcgggcg agtgggggtg aagtgtgggc ggtggaaccc gacggcggag      60
caggtgaagg tcctgacgga gctgttccga gcggggttgc ggacgccgag cacggagcag     120
atccagcgca tctccactca cctcagcgca ttcggcaagg tggagagcaa gaacgtcttc     180
tactggttcc agaaccacaa ggcccgcgag cgccaccacc acaagaagcg ccgccgcggc     240
gcctcctccc ccgacagcgg cagcaacgat gacgatggcc gcgccgcagc ccacgagggc     300
gacgccgacc tcgtcctgca gcctcctgag agcaagcggg aggccagaag ctacggccat     360
catcaccggc tcatgacatg taagcataca tactttgatt aattatttcg cctatataca     420
tgcatacgta cgcatgaata cccatgatcg aatagctgat caagttgctg ttcgatccgc     480
gcttgcaggc tacgtgaggg atgtggtgga gacggaagcg atgtgggagc ggccgacgag     540
ggaggtggaa acgctggagc tgttcccact caagtcgtat gacctcgagg tggacaaggt     600
ccggtatgtg aggggcggcg gtggcgagca gtgcagggag atctcgttct tcgacgtcgc     660
```
tgccggccgg gatccgccgc tggagctcag gctttgcagc ttcggcctct ag          712

<210> SEQ ID NO 4
<211> LENGTH: 200
<212> TYPE: PRT
<213> ORGANISM: rice

<400> SEQUENCE: 4

Met Glu Ala Leu Ser Gly Arg Val Gly Val Lys Cys Gly Arg Trp Asn
1               5                   10                  15

Pro Thr Ala Glu Gln Val Lys Val Leu Thr Glu Leu Phe Arg Ala Gly
            20                  25                  30

Leu Arg Thr Pro Ser Thr Glu Gln Ile Gln Arg Ile Ser Thr His Leu
        35                  40                  45

Ser Ala Phe Gly Lys Val Glu Ser Lys Asn Val Phe Tyr Trp Phe Gln
    50                  55                  60

Asn His Lys Ala Arg Glu Arg His His Lys Lys Arg Arg Arg Gly
65                  70                  75                  80

Ala Ser Ser Pro Asp Ser Gly Ser Asn Asp Asp Gly Arg Ala Ala
                85                  90                  95

Ala His Glu Gly Asp Ala Asp Leu Val Leu Gln Pro Pro Glu Ser Lys
            100                 105                 110

Arg Glu Ala Arg Ser Tyr Gly His His His Arg Leu Met Thr Cys Tyr
        115                 120                 125

Val Arg Asp Val Val Glu Thr Glu Ala Met Trp Glu Arg Pro Thr Arg
    130                 135                 140

Glu Val Glu Thr Leu Glu Leu Phe Pro Leu Lys Ser Tyr Asp Leu Glu
145                 150                 155                 160

Val Asp Lys Val Arg Tyr Val Arg Gly Gly Gly Glu Gln Cys Arg
                165                 170                 175

Glu Ile Ser Phe Phe Asp Val Ala Ala Gly Arg Asp Pro Pro Leu Glu
            180                 185                 190

Leu Arg Leu Cys Ser Phe Gly Leu
        195                 200

<210> SEQ ID NO 5
<211> LENGTH: 22
<212> TYPE: DNA
<213> ORGANISM: Artificial Sequence
<220> FEATURE:
<223> OTHER INFORMATION: Forward primer for Wheat TAWOX5 Gene Cloning

<400> SEQUENCE: 5
gtgtcaatgg aggcgctgag cg                                          22

<210> SEQ ID NO 6
<211> LENGTH: 22
<212> TYPE: DNA
<213> ORGANISM: Artificial Sequence
<220> FEATURE:
<223> OTHER INFORMATION: Reverse primer for Wheat TAWOX5 Gene Cloning

<400> SEQUENCE: 6
gtgtcaatgg aggcgctgag cg                                          22

<210> SEQ ID NO 7
<211> LENGTH: 26
<212> TYPE: DNA
<213> ORGANISM: Artificial Sequence

```
<220> FEATURE:
<223> OTHER INFORMATION: Wox5SmaF primer

<400> SEQUENCE: 7
aaacccggga tggaggcgct gagcgg                                              26

<210> SEQ ID NO 8
<211> LENGTH: 26
<212> TYPE: DNA
<213> ORGANISM: Artificial Sequence
<220> FEATURE:
<223> OTHER INFORMATION: Wox5KpnR primer

<400> SEQUENCE: 8
aaaggtacct tagaccagat accgat                                              26

<210> SEQ ID NO 9
<211> LENGTH: 22
<212> TYPE: DNA
<213> ORGANISM: Artificial Sequence
<220> FEATURE:
<223> OTHER INFORMATION: Forward Bar primer

<400> SEQUENCE: 9
accatcgtca accactacat cg                                                  22

<210> SEQ ID NO 10
<211> LENGTH: 21
<212> TYPE: DNA
<213> ORGANISM: Artificial Sequence
<220> FEATURE:
<223> OTHER INFORMATION: Reverse Bar primer

<400> SEQUENCE: 10
gctgccagaa accacgtcat g                                                   21

<210> SEQ ID NO 11
<211> LENGTH: 633
<212> TYPE: DNA
<213> ORGANISM: Triticum aestivum

<400> SEQUENCE: 11
atggaggcgc tgagcgggcg ggtgggagtg aagtgcgggc ggtggaaccc gacggcggag         60
caggtgaagg tgctgacgga gctgttccgg gcggggctgc ggacgccgag caccgagcag        120
atccagcgga tctccaccca cctcagcgcc ttcggcaagg tggagagcaa gaacgtcttc        180
tactggttcc agaaccacaa ggcccgcgag cgccaccacc acaagaagcg ccgccgcgtc        240
gcatcctgct cccccgacag cagcagcaac gatgaagaga ccggccgtgc cgccgccgcc        300
gagcccgccg acctcgtgct ccagcctccc gagagcaagg ggaggccgg aggctacaac         360 caccaccccc ggatcatgac atgctatgtg agggaggtgg cggagcagga agaggcgacg        420
acgtgggagc ggccgacgag ggaagtggag acgctggagc tgttcccgct caaagcagcc        480
tgctacgacc tggagctgga ggcggacagg ttcagccggt atgtgaggag cggcgagcaa        540
cagtgcaggg agatctcctt cttcgacgtg gccaccggac gggatccgcc gctggagctc        600
aggctctgca gcttcgatcg gtatctggtc taa                                     633

<210> SEQ ID NO 12
<211> LENGTH: 603
<212> TYPE: DNA
<213> ORGANISM: rice
```

<400> SEQUENCE: 12

```
atggaggctc ttagcgggcg agtggggtg aagtgtgggc ggtggaaccc gacggcggag      60
caggtgaagg tcctgacgga gctgttccga gcggggttgc ggacgccgag cacggagcag     120
atccagcgca tctccactca cctcagcgca ttcggcaagg tggagagcaa gaacgtcttc     180
tactggttcc agaaccacaa gcccgcgag cgccaccacc acaagaagcg ccgccgcggc     240
gcctcctccc ccgacagcgg cagcaacgat gacgatggcc gcgccgcagc ccacgagggc     300
gacgccgacc tcgtcctgca gcctcctgag agcaagcggg aggccagaag ctacggccat     360
catcaccggc tcatgacatg ctacgtgagg gatgtggtgg agacgaagc gatgtgggag     420
cggccgacga gggaggtgga aacgctggag ctgttcccac tcaagtcgta tgacctcgag     480
gtggacaagg tccggtatgt gagggggcggc ggtggcgagc agtgcaggga gatctcgttc     540
ttcgacgtcg ctgccggccg ggatccgccg ctggagctca ggctttgcag cttcggcctc     600
tag                                                                    603
```

<210> SEQ ID NO 13
<211> LENGTH: 50
<212> TYPE: DNA
<213> ORGANISM: Artificial Sequence
<220> FEATURE:
<223> OTHER INFORMATION: TaWox5-FW primer

<400> SEQUENCE: 13

```
ggggacaagt ttgtacaaaa aagcaggcta tggaggcgct gagcgggcgg             50
```

<210> SEQ ID NO 14
<211> LENGTH: 50
<212> TYPE: DNA
<213> ORGANISM: Artificial Sequence
<220> FEATURE:
<223> OTHER INFORMATION: TaWox5-RV primer

<400> SEQUENCE: 14

```
ggggaccact ttgtacaaga aagctgggtt tagaccagat accgatcgaa             50
```

<210> SEQ ID NO 15
<211> LENGTH: 52
<212> TYPE: DNA
<213> ORGANISM: Artificial Sequence
<220> FEATURE:
<223> OTHER INFORMATION: osTaWox5-FW primer

<400> SEQUENCE: 15

```
ggggaccact ttgtacaaga aagctgggtc tagaggccga agctgcaaag cc          52
```

<210> SEQ ID NO 16
<211> LENGTH: 52
<212> TYPE: DNA
<213> ORGANISM: Artificial Sequence
<220> FEATURE:
<223> OTHER INFORMATION: osTaWox5-RV primer

<400> SEQUENCE: 16

```
ggggaccact ttgtacaaga aagctgggtc tagaggccga agctgcaaag cc          52
```

<210> SEQ ID NO 17
<211> LENGTH: 36
<212> TYPE: DNA
<213> ORGANISM: Artificial Sequence
<220> FEATURE:
<223> OTHER INFORMATION: GFPbamFinf4 primer

```
<400> SEQUENCE: 17
caggtcgact ctagaggaat ggtgagcaag ggcgag                                36

<210> SEQ ID NO 18
<211> LENGTH: 67
<212> TYPE: DNA
<213> ORGANISM: Artificial Sequence
<220> FEATURE:
<223> OTHER INFORMATION: GFPbamRinf4 primer

<400> SEQUENCE: 18
ttcgagctcg gtacccgggg atccaccacc gccacctccg ccaccgcctc cagatctgta    60
cagctcg                                                              67

<210> SEQ ID NO 19
<211> LENGTH: 35
<212> TYPE: DNA
<213> ORGANISM: Artificial Sequence
<220> FEATURE:
<223> OTHER INFORMATION: Wox5bamFinf3 primer

<400> SEQUENCE: 19
caggtcgact ctagaggaat ggaggcgctg agcgg                               35

<210> SEQ ID NO 20
<211> LENGTH: 65
<212> TYPE: DNA
<213> ORGANISM: Artificial Sequence
<220> FEATURE:
<223> OTHER INFORMATION: Wox5bamRinf3 primer

<400> SEQUENCE: 20
ttcgagctcg gtacccgggg atccaccacc gccacctccg ccaccgcctc cgaccagata    60
ccgat                                                                65

<210> SEQ ID NO 21
<211> LENGTH: 37
<212> TYPE: DNA
<213> ORGANISM: Artificial Sequence
<220> FEATURE:
<223> OTHER INFORMATION: Wox5Finf4 primer

<400> SEQUENCE: 21
gcggaggtgg cggtggtgga atggaggcgc tgagcgg                             37

<210> SEQ ID NO 22
<211> LENGTH: 38
<212> TYPE: DNA
<213> ORGANISM: Artificial Sequence
<220> FEATURE:
<223> OTHER INFORMATION: Wox5Rinf4 primer

<400> SEQUENCE: 22
ttcgagctcg gtacccgggg attagaccag ataccgat                            38

<210> SEQ ID NO 23
<211> LENGTH: 38
<212> TYPE: DNA
<213> ORGANISM: Artificial Sequence
<220> FEATURE:
<223> OTHER INFORMATION: GFPFinf3 primer

<400> SEQUENCE: 23
```

```
gcggaggtgg cggtggtgga atggtgagca agggcgag                                    38

<210> SEQ ID NO 24
<211> LENGTH: 40
<212> TYPE: DNA
<213> ORGANISM: Artificial Sequence
<220> FEATURE:
<223> OTHER INFORMATION: GFPRinf3 primer

<400> SEQUENCE: 24
ttcgagctcg gtacccgggg attaagatct gtacagctcg                                  40
```